US005246852A

United States Patent [19]

Payne et al.

[11] Patent Number: 5,246,852

[45] Date of Patent: Sep. 21, 1993

[54] BACILLUS THURINGIENSIS ISOLATE ACTIVE AGAINST LEPIDOPTERAN PESTS, AND GENES ENCODING NOVEL LEPIDOPTERAN-ACTIVE TOXINS

[75] Inventors: Jewel Payne; August J. Sick, both of San Diego, Calif.

[73] Assignee: Mycogen Corporation, San Diego, Calif.

[21] Appl. No.: 714,413

[22] Filed: Jun. 12, 1991

Related U.S. Application Data

[62] Division of Ser. No. 371,955, Jun. 27, 1989, Pat. No. 5,126,133.

[51] Int. Cl.[5] .................... C12N 1/21; C12N 15/32; C12N 15/70; A01N 63/00

[52] U.S. Cl. .................... 435/252.31; 435/69.1; 435/172.3; 435/252.3; 435/252.33; 435/252.34; 435/252.35; 435/320.1; 424/93 A; 536/23.71

[58] Field of Search .................... 435/69.1, 71.1, 91, 435/172.1, 172.3, 252.1, 252.3, 252.31, 252.34, 252.35, 320.1; 424/93; 935/6, 9, 22, 59, 60, 61, 64; 536/27

[56] References Cited

U.S. PATENT DOCUMENTS 4,771,131 9/1968 Herrnsstadt et al. ............ 536/23.71

OTHER PUBLICATIONS

Yamamoto et al., (Jun. 20, 1988), Chemical Abstracts, vol. 108, (25), Abstract No. 217068m, Curr Microbiol., 1988 (17)(1), 5-12.

Shimizu et al., 1988, Agric. Biol. Chem., 52(6):1565-1573.

Masson et al., (Jan. 11, 1989), NAR, 17(1):446.

Schnopf et al., 1985, J. Biol. Chem., 260(10):6264-6272.

Honée et al., 1988, NAR, 16(13):6240.

*Primary Examiner*—Richard A. Schwartz

*Assistant Examiner*—J. LeGuyader

*Attorney, Agent, or Firm*—Saliwanchik & Saliwanchik

[57] ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

42 Claims, 64 Drawing Sheets

```
                    5                  10                  15
  1 Met Glu Ile Met Asn Asn Gln Asn Gln Cys Val Pro Tyr Asn Cys
 16 Leu Asn Asp Pro Thr Ile Glu Ile Leu Glu Gly Glu Arg Ile Glu
 31 Thr Gly Tyr Thr Pro Ile Asp Ile Ser Leu Ser Leu Thr Gln Phe
 46 Leu Leu Ser Glu Phe Val Pro Gly Ala Gly Phe Val Leu Gly Leu
 61 Ile Asp Leu Ile Trp Gly Phe Val Gly Pro Ser Gln Trp Asp Ala
 76 Phe Leu Val Gln Ile Glu Gln Leu Ile Asn Gln Arg Ile Glu Glu
 91 Phe Ala Arg Asn Gln Ala Ile Ser Arg Leu Glu Gly Leu Ser Asn
106 Leu Tyr Gln Ile Tyr Ala Glu Ala Phe Arg Glu Trp Glu Ala Asp
121 Pro Thr Asn Pro Ala Leu Thr Glu Glu Met Arg Ile Gln Phe Asn
136 Asp Met Asn Ser Ala Leu Thr Thr Ala Ile Pro Leu Phe Thr Val
151 Gln Asn Tyr Gln Val Pro Leu Leu Ser Val Tyr Val Gln Ala Ala
166 Asn Leu His Leu Ser Val Leu Arg Asp Val Ser Val Phe Gly Gln
181 Arg Trp Gly Phe Asp Val Ala Thr Ile Asn Ser Arg Tyr Asn Asp
196 Leu Thr Arg Leu Ile Gly Thr Tyr Thr Asp Tyr Ala Val Arg Trp
211 Tyr Asn Thr Gly Leu Glu Arg Val Trp Gly Pro Asp Ser Arg Asp
```

```
                    5                  10                  15
  1 Met Glu Ile Asn Asn Gln Asn Gln Cys Val Pro Tyr Asn Cys Leu
 16 Ser Asn Pro Lys Glu Ile Ile Leu Gly Glu Glu Arg Leu Glu Thr
 31 Gly Asn Thr Val Ala Asp Ile Ser Leu Gly Leu Ile Asn Phe Leu
 46 Tyr Ser Asn Phe Val Pro Gly Gly Gly Phe Ile Val Gly Leu Leu
 61 Glu Leu Ile Trp Gly Phe Ile Gly Pro Ser Gln Trp Asp Ile Phe
 76 Leu Ala Gln Ile Glu Gln Leu Ile Ser Gln Arg Ile Glu Glu Phe
 91 Ala Arg Asn Gln Ala Ile Ser Arg Leu Glu Gly Leu Ser Asn Leu
106 Tyr Lys Val Tyr Val Arg Ala Phe Ser Asp Trp Glu Lys Asp Pro
121 Thr Asn Pro Ala Leu Arg Glu Glu Met Arg Ile Gln Phe Asn Asp
136 Met Asn Ser Ala Leu Ile Thr Ala Ile Pro Leu Phe Arg Val Gln
151 Asn Tyr Glu Val Ala Leu Leu Ser Val Tyr Val Gln Ala Ala Asn
166 Leu His Leu Ser Ile Leu Arg Asp Val Ser Val Phe Gly Glu Arg
181 Trp Gly Tyr Asp Thr Ala Thr Ile Asn Asn Arg Tyr Ser Asp Leu
196 Thr Ser Leu Ile His Val Tyr Thr Asn His Cys Val Asp Thr Tyr
211 Asn Gln Gly Leu Arg Arg Leu Glu Gly Arg Phe Leu Ser Asp Trp
```

```
                    5                  10                  15
  1 Met Glu Glu Asn Asn Gln Asn Gln Cys Ile Pro Tyr Asn Cys Leu
 16 Ser Asn Pro Glu Glu Val Leu Leu Asp Gly Glu Arg Ile Ser Thr
 31 Gly Asn Ser Ser Ile Asp Ile Ser Leu Ser Leu Val Gln Phe Leu
 46 Val Ser Asn Phe Val Pro Gly Gly Gly Phe Leu Val Gly Leu Ile
 61 Asp Phe Val Trp Gly Ile Val Gly Pro Ser Gln Trp Asp Ala Phe
 76 Leu Val Gln Ile Glu Gln Leu Ile Asn Glu Arg Ile Ala Glu Phe
 91 Ala Arg Asn Ala Ala Ile Ala Asn Leu Glu Gly Leu Gly Asn Asn
106 Phe Asn Ile Tyr Val Glu Ala Phe Lys Glu Trp Glu Glu Asp Pro
121 Asn Asn Pro Ala Thr Arg Thr Arg Val Ile Asp Arg Phe Arg Ile
136 Leu Asp Gly Leu Leu Glu Arg Asp Ile Pro Ser Phe Arg Ile Ser
151 Gly Phe Glu Val Pro Leu Leu Ser Val Tyr Ala Gln Ala Ala Asn
166 Leu His Leu Ala Ile Leu Arg Asp Ser Val Ile Phe Gly Glu Arg
181 Trp Gly Leu Thr Thr Ile Asn Val Asn Glu Asn Tyr Asn Arg Leu
196 Ile Arg His Ile Asp Glu Tyr Ala Asp His Cys Ala Asn Thr Tyr
211 Asn Arg Gly Leu Asn Asn Leu Pro Lys Ser Thr Tyr Gln Asp Trp
```

```
             10         20         30         40         50         60
  1 ATGGAGATAA TGAATAATCA GAATCAATGC GTTCCTTATA ACTGTTTGAA TGATCCGACA
 61 ATTGAAATAT TAGAAGGAGA AAGAATAGAA ACTGGTTACA CCCCAATAGA TATTTCCTTG
121 TCGCTAACGC AATTTCTGTT GAGTGAATTT GTCCCAGGTG CTGGGTTTGT ATTAGGTTTA
181 ATTGATTTAA TATGGGGGTT TGTGGGTCCC TCTCAATGGG ATGCATTTCT TGTGCAAATT
241 GAACAGTTAA TTAACCAAAG AATAGAGGAA TTCGCTAGGA ACCAAGCAAT TTCTAGATTA

            310        320        330        340        350        360
301 GAAGGGCTAA GCAACCTTTA TCAAATTTAC GCAGAAGCTT TTAGAGAGTG GGAAGCAGAT
361 CCTACTAATC CAGCATTAAC AGAAGAGATG CGTATTCAGT TCAATGACAT GAACAGTGCT
421 CTTACAACCG CTATTCCTCT TTTTACAGTT CAAAATTATC AAGTACCTCT TCTATCAGTA
481 TATGTTCAAG CTGCAAATTT ACATTTATCG GTTTTGAGAG ATGTTTCAGT GTTTGGACAA
541 CGTTGGGGAT TTGATGTAGC AACAATCAAT AGTCGTTATA ATGATTTAAC TAGGCTTATT

            610        620        630        640        650        660
601 GGCACCTATA CAGATTATGC TGTACGCTGG TATAATACGG GATTAGAACG TGTATGGGGA
661 CCGGATTCTA GAGATTGGGT AAGGTATAAT CAATTTAGAA GAGAGCTAAC ACTAACTGTA
721 TTAGATATCG TTTCTCTGTT CCCGAACTAT GATAGTAGAA CGTATCCAAT TCGAACAGTT
781 TCCCAATTAA CTAGAGAAAT TTATACAAAC CCAGTATTAG AAAATTTTGA TGGTAGTTTT
841 CGTGGAATGG CTCAGAGAAT AGAACAGAAT ATTAGGCAAC CACATCTTAT GGATCTCCTT
```

Figure 2A

```
             910        920        930        940        950        960
 901 AATAGTATAA CCATTTATAC TGATGTGCAT AGAGGCTTTA ATTATTGGTC AGGACATCAA
 961 ATAACAGCTT CTCCTGTCGG TTTTGCGGGG CCAGAATTTA CTTTTCCTAG ATATGGAACC
1021 ATGGGAAATG CTGCTCCACC CGTACTGATC TCAACTACTG GTTTGGGGAT TTTTAGAACA
1081 TTATCTTCAC CTCTTTACAG AAGAATTATA CTTGGTTCAG GCCCAAATAA TCAGAACCTG
1141 TTTGTCCTTG ATGGAACGGA ATTTTCTTTT GCCTCCCTAA CAGCCGATTT ACCTTCTACT

            1210       1220       1230       1240       1250       1260
1201 ATATACAGAC AAAGGGGAAC GGTCGATTCA CTAGATGTAA TACCGCCACA GGATAATAGT
1261 GTGCCAGCAC GTGCGGGATT TAGTCATCGA TTAAGTCATG TTACAATGCT GAGCCAAGCA
1321 GCTGGAGCAG TTTACACCTT GAGAGCTCCA ACGTTTTCTT GGCGACATCG TAGTGCTGAA
1381 TTCTCTAACC TAATTCCTTC ATCACAAATC ACACAGATAC CTTTAACAAA GTCTATTAAT
1441 CTTGGCTCTG GGACCTCTGT TGTTAAAGGA CCAGGATTTA CAGGAGGAGA TATTCTTCGA

            1510       1520       1530       1540       1550       1560
1501 AGAACTTCAC CTGGCCAGAT TTCAACCTTA AGAGTGACTA TTACTGCACC ATTATCACAA
1561 AGATATCGCG TAAGAATTCG CTACGCTTCT ACTACAAATT TACAATTCCA TACATCAATT
1621 GACGGAAGAC CTATTAATCA GGGGAATTTT TCAGCAACTA TGAGTAGTGG GGGTAATTTA
1681 CAGTCCGGAA GCTTTAGGAC TGCAGGTTTT ACTACTCCGT TTAACTTTTC AAATGGATCA
1741 AGTATATTTA CGTTAAGTGC TCATGTCTTC AATTCAGGCA ATGAAGTTTA TATAGATCGA
```

Figure 2B

```
                1810       1820       1830       1840       1850       1860
1801  ATTGAATTTG TTCCGGCAGA AGTAACATTT GAGGCGGAAT ATGATTTAGA AAGAGCGCAA
1861  GAGGCGGTGA ATGCTCTGTT TACTTCTTCC AATCAACTAG GATTAAAAAC AAATGTGACG
1921  GACTATCATA TTGATCAAGT GTCCAATCTA GTCGAATGTT TATCCGGTGA ATTCTGTCTG
1981  GATGAAAAGA GAGAATTGTC CGAGAAAGTC AAACATGCGA AGCGACTCAG TGATGAGCGG
2041  AATTTACTTC AAGACCCAAA CTTCAGAGGC ATCAATAGAC AACCAGACCG TGGCTGGAGA

                2110       2120       2130       2140       2150       2160
2101  GGCAGTACGG ATATTACCAT CCAAGGAGGA GATGACGTAT TCAAAGAGAA TTACGTCACA
2161  CTACCGGGTA CCTTTAATGA GTGTTATCCT ACGTATCTGT ATCAAAAAAT AGATGAGTCG
2221  AAATTAAAAG CCTATACCCG TTACCAATTA AGAGGGTACA TCGAGGATAG TCAAGACTTA
2281  GAAATCTATT TAATTCGCTA CAATACAAAA CACGAAACAG TAAATGTGCC AGGTACGGGT
2341  TCCTTATGGC CGCTTTCAGT CGAAAATCCA ATTGGAAAGT GCGGAGAACC AAATCGATGC

                2410       2420       2430       2440       2450       2460
2401  GCACCACAAC TTGAATGGAA TCCTGATCTA GATTGTTCCT GCAGAGACGG GGAAAAATGT
2461  GCACATCACT CCCATCATTT CTCCTTGGAC ATTGATATTG GATGTACAGA TTTAAATGAG
2521  AACTTAGGTG TATGGGTGAT ATTCAAAATT AAGACGCAAG ATGGTCACGC AAGACTAGGT
2581  AATCTAGAGT TTCTCGAAGA GAAACCATTA GTAGGCGAAT CGTTAGCACG CGTGAAGAGA
2641  GCGGAGAAGA AGTGGAGAGA CAAACGAGAG AAATTGCAAG TGGAAACAAA TATCGTTTAT
```

Figure 2C

```
                2710       2720       2730       2740       2750       2760
2701 AAAGAGGCAA AAGAATCTGT AGATGCTTTA TTTGTGAACT CTCAATATGA TAGATTACAA
2761 GCGGATACCG ACATCGCGAT GATTCATGCG GCAGATAAAC GCGTTCATCG AATTCGAGAA
2821 GCATATCTTC CAGAGTTATC TGTAATTCCG GGTGTCAATG CGGGCATTTT TGAAGAATTA
2881 GAGGGACGTA TTTTCACAGC CTACTCTTTA TATGATGCGA GAAATGTCAT TAAAAATGGC
2941 GATTTCAATA ATGGCTTATC ATGCTGGAAC GTGAAAGGGC ATGTAGATGT AGAAGAACAA

                3010       3020       3030       3040       3050       3060
3001 AACAACCACC GTTCGGTTCT TGTTGTCCCG GAATGGGAAG CAGAGGTGTC ACAAGAGGTT
3061 CGTGTCTGTC CAGGTCGTGG CTATATCCTA CGTGTTACAG CGTACAAAGA GGGATATGGA
3121 GAAGGTTGCG TAACGATTCA TGAGATCGAA GACAATACAG ACGAACTGAA ATTCAGCAAC
3181 TGTGTAGAAG AGGAAGTATA TCCAAACAAC ACGGTAACGT GTAATGATTA TACTGCAAAT
3241 CAAGAAGAAT ACGGGGGTGC GTACACTTCT CGTAATCGTG GATATGGTGA ATCTTATGAA

                3310       3320       3330       3340       3350       3360
3301 AGTAATTCTT CCATACCAGC TGAGTATGCG CCAGTTTATG AGGAAGCATA TATAGATGGA
3361 AGAAAAGAGA ATCCTTGTGA ATCTAACAGA GGATATGGGG ATTACACGCC ACTACCAGCT
3421 GGTTATGTGA CAAAAGAATT AGAGTACTTC CCAGAAACCG ATAAGGTATG GATTGAGATC
3481 GGGGAAACGG AAGGAACATT CATCGTGGAT AGCGTGGAAT TACTCCTTAT GGAGGAA*
```

Segment 1-*

Figure 2D

```
                          5                                10                                15
  1 Met Glu Ile Met Asn Asn Gln Asn Gln Cys Val Pro Tyr Asn Cys
 16 Leu Asn Asp Pro Thr Ile Glu Ile Leu Glu Gly Glu Arg Ile Glu
 31 Thr Gly Tyr Thr Pro Ile Asp Ile Ser Leu Ser Leu Thr Gln Phe
 46 Leu Leu Ser Glu Phe Val Pro Gly Ala Gly Phe Val Leu Gly Leu
 61 Ile Asp Leu Ile Trp Gly Phe Val Gly Pro Ser Gln Trp Asp Ala
 76 Phe Leu Val Gln Ile Glu Gln Leu Ile Asn Gln Arg Ile Glu Glu
 91 Phe Ala Arg Asn Gln Ala Ile Ser Arg Leu Glu Gly Leu Ser Asn
106 Leu Tyr Gln Ile Tyr Ala Glu Ala Phe Arg Glu Trp Glu Ala Asp
121 Pro Thr Asn Pro Ala Leu Thr Glu Glu Met Arg Ile Gln Phe Asn
136 Asp Met Asn Ser Ala Leu Thr Thr Ala Ile Pro Leu Phe Thr Val
151 Gln Asn Tyr Gln Val Pro Leu Leu Ser Val Tyr Val Gln Ala Ala
166 Asn Leu His Leu Ser Val Leu Arg Asp Val Ser Val Phe Gly Gln
181 Arg Trp Gly Phe Asp Val Ala Thr Ile Asn Ser Arg Tyr Asn Asp
196 Leu Thr Arg Leu Ile Gly Thr Tyr Thr Asp Tyr Ala Val Arg Trp
211 Tyr Asn Thr Gly Leu Glu Arg Val Trp Gly Pro Asp Ser Arg Asp
```

Figure 3A

```
226 Trp Val Arg Tyr Asn Gln Phe Arg Arg Glu Leu Thr Leu Thr Val
241 Leu Asp Ile Val Ser Leu Phe Pro Asn Tyr Asp Ser Arg Thr Tyr
256 Pro Ile Arg Thr Val Ser Gln Leu Thr Arg Glu Ile Tyr Thr Asn
271 Pro Val Leu Glu Asn Phe Asp Gly Ser Phe Arg Gly Met Ala Gln
286 Arg Ile Glu Gln Asn Ile Arg Gln Pro His Leu Met Asp Leu Leu
301 Asn Ser Ile Thr Ile Tyr Thr Asp Val His Arg Gly Phe Asn Tyr
316 Trp Ser Gly His Gln Ile Thr Ala Ser Pro Val Gly Phe Ala Gly
331 Pro Glu Phe Thr Phe Pro Arg Tyr Gly Thr Met Gly Asn Ala Ala
346 Pro Pro Val Leu Ile Ser Thr Thr Gly Leu Gly Ile Phe Arg Thr
361 Leu Ser Ser Pro Leu Tyr Arg Arg Ile Ile Leu Gly Ser Gly Pro
376 Asn Asn Gln Asn Leu Phe Val Leu Asp Gly Thr Glu Phe Ser Phe
391 Ala Ser Leu Thr Ala Asp Leu Pro Ser Thr Ile Tyr Arg Gln Arg
406 Gly Thr Val Asp Ser Leu Asp Val Ile Pro Pro Gln Asp Asn Ser
421 Val Pro Ala Arg Ala Gly Phe Ser His Arg Leu Ser His Val Thr
436 Met Leu Ser Gln Ala Ala Gly Ala Val Tyr Thr Leu Arg Ala Pro
```

Figure 3B

```
451 Thr Phe Ser Trp Arg His Arg Ser Ala Glu Phe Ser Asn Leu Ile
466 Pro Ser Ser Gln Ile Thr Gln Ile Pro Leu Thr Lys Ser Ile Asn
481 Leu Gly Ser Gly Thr Ser Val Val Lys Gly Pro Gly Phe Thr Gly
496 Gly Asp Ile Leu Arg Arg Thr Ser Pro Gly Gln Ile Ser Thr Leu
511 Arg Val Thr Ile Thr Ala Pro Leu Ser Gln Arg Tyr Arg Val Arg
526 Ile Arg Tyr Ala Ser Thr Thr Asn Leu Gln Phe His Thr Ser Ile
541 Asp Gly Arg Pro Ile Asn Gln Gly Asn Phe Ser Ala Thr Met Ser
556 Ser Gly Gly Asn Leu Gln Ser Gly Ser Phe Arg Thr Ala Gly Phe
571 Thr Thr Pro Phe Asn Phe Ser Asn Gly Ser Ser Ile Phe Thr Leu
586 Ser Ala His Val Phe Asn Ser Gly Asn Glu Val Tyr Ile Asp Arg
601 Ile Glu Phe Val Pro Ala Glu Val Thr Phe Glu Ala Glu Tyr Asp
616 Leu Glu Arg Ala Gln Glu Ala Val Asn Ala Leu Phe Thr Ser Ser
631 Asn Gln Leu Gly Leu Lys Thr Asn Val Thr Asp Tyr His Ile Asp
646 Gln Val Ser Asn Leu Val Glu Cys Leu Ser Gly Glu Phe Cys Leu
661 Asp Glu Lys Arg Glu Leu Ser Glu Lys Val Lys His Ala Lys Arg
```

Figure 3C

```
676 Leu Ser Asp Glu Arg Asn Leu Leu Gln Asp Pro Asn Phe Arg Gly
691 Ile Asn Arg Gln Pro Asp Arg Gly Trp Arg Gly Ser Thr Asp Ile
706 Thr Ile Gln Gly Gly Asp Asp Val Phe Lys Glu Asn Tyr Val Thr
721 Leu Pro Gly Thr Phe Asn Glu Cys Tyr Pro Thr Tyr Leu Tyr Gln
736 Lys Ile Asp Glu Ser Lys Leu Lys Ala Tyr Thr Arg Tyr Gln Leu
751 Arg Gly Tyr Ile Glu Asp Ser Gln Asp Leu Glu Ile Tyr Leu Ile
766 Arg Tyr Asn Thr Lys His Glu Thr Val Asn Val Pro Gly Thr Gly
781 Ser Leu Trp Pro Leu Ser Val Glu Asn Pro Ile Gly Lys Cys Gly
796 Glu Pro Asn Arg Cys Ala Pro Gln Leu Glu Trp Asn Pro Asp Leu
811 Asp Cys Ser Cys Arg Asp Gly Glu Lys Cys Ala His His Ser His
826 His Phe Ser Leu Asp Ile Asp Ile Gly Cys Thr Asp Leu Asn Glu
841 Asn Leu Gly Val Trp Val Ile Phe Lys Ile Lys Thr Gln Asp Gly
856 His Ala Arg Leu Gly Asn Leu Glu Phe Leu Glu Glu Lys Pro Leu
871 Val Gly Glu Ser Leu Ala Arg Val Lys Arg Ala Glu Lys Lys Trp
886 Arg Asp Lys Arg Glu Lys Leu Gln Val Glu Thr Asn Ile Val Tyr
```

Figure 3D

901 Lys Glu Ala Lys Glu Ser Val Asp Ala Leu Phe Val Asn Ser Gln

916 Tyr Asp Arg Leu Gln Ala Asp Thr Asp Ile Ala Met Ile His Ala

931 Ala Asp Lys Arg Val His Arg Ile Arg Glu Ala Tyr Leu Pro Glu

946 Leu Ser Val Ile Pro Gly Val Asn Ala Gly Ile Phe Glu Glu Leu

961 Glu Gly Arg Ile Phe Thr Ala Tyr Ser Leu Tyr Asp Ala Arg Asn

976 Val Ile Lys Asn Gly Asp Phe Asn Asn Gly Leu Ser Cys Trp Asn

991 Val Lys Gly His Val Asp Val Glu Glu Gln Asn Asn His Arg Ser

1006 Val Leu Val Val Pro Glu Trp Glu Ala Glu Val Ser Gln Glu Val

1021 Arg Val Cys Pro Gly Arg Gly Tyr Ile Leu Arg Val Thr Ala Tyr

1036 Lys Glu Gly Tyr Gly Glu Gly Cys Val Thr Ile His Glu Ile Glu

1051 Asp Asn Thr Asp Glu Leu Lys Phe Ser Asn Cys Val Glu Glu Glu

1066 Val Tyr Pro Asn Asn Thr Val Thr Cys Asn Asp Tyr Thr Ala Asn

1081 Gln Glu Glu Tyr Gly Gly Ala Tyr Thr Ser Arg Asn Arg Gly Tyr

1096 Gly Glu Ser Tyr Glu Ser Asn Ser Ser Ile Pro Ala Glu Tyr Ala

1111 Pro Val Tyr Glu Glu Ala Tyr Ile Asp Gly Arg Lys Glu Asn Pro

1126 Cys Glu Ser Asn Arg Gly Tyr Gly Asp Tyr Thr Pro Leu Pro Ala

1141 Gly Tyr Val Thr Lys Glu Leu Glu Tyr Phe Pro Glu Thr Asp Lys

1156 Val Trp Ile Glu Ile Gly Glu Thr Glu Gly Thr Phe Ile Val Asp

1171 Ser Val Glu Leu Leu Leu Met Glu Glu

Fragment 1-*

Figure 3E

```
                     5                       10                          15                      20
Met Glu Ile Met Asn Asn Gln Asn Gln Cys Val Pro Tyr Asn Cys Leu Asn Asp Pro Thr
ATG GAG ATA ATG AAT AAT CAG AAT CAA TGC GTT CCT TAT AAC TGT TTG AAT GAT CCG ACA

                    25                       30                          35                      40
Ile Glu Ile Leu Glu Gly Glu Arg Ile Glu Thr Gly Tyr Thr Pro Ile Asp Ile Ser Leu
ATT GAA ATA TTA GAA GGA GAA AGA ATA GAA ACT GGT TAC ACC CCA ATA GAT ATT TCC TTG

                    45                       50                          55                      60
Ser Leu Thr Gln Phe Leu Leu Ser Glu Phe Val Pro Gly Ala Gly Phe Val Leu Gly Leu
TCG CTA ACG CAA TTT CTG TTG AGT GAA TTT GTC CCA GGT GCT GGG TTT GTA TTA GGT TTA

                    65                       70                          75                      80
Ile Asp Leu Ile Trp Gly Phe Val Gly Pro Ser Gln Trp Asp Ala Phe Leu Val Gln Ile
ATT GAT TTA ATA TGG GGG TTT GTG GGT CCC TCT CAA TGG GAT GCA TTT CTT GTG CAA ATT

                    85                       90                          95                     100
Glu Gln Leu Ile Asn Gln Arg Ile Glu Glu Phe Ala Arg Asn Gln Ala Ile Ser Arg Leu
GAA CAG TTA ATT AAC CAA AGA ATA GAG GAA TTC GCT AGG AAC CAA GCA ATT TCT AGA TTA
```

Figure 4A

```
                    105                 110                 115                 120
Glu Gly Leu Ser Asn Leu Tyr Gln Ile Tyr Ala Glu Ala Phe Arg Glu Trp Glu Ala Asp
GAA GGG CTA AGC AAC CTT TAT CAA ATT TAC GCA GAA GCT TTT AGA GAG TGG GAA GCA GAT

                    125                 130                 135                 140
Pro Thr Asn Pro Ala Leu Thr Glu Glu Met Arg Ile Gln Phe Asn Asp Met. Asn Ser Ala
CCT ACT AAT CCA GCA TTA ACA GAA GAG ATG CGT ATT CAG TTC AAT GAC ATG AAC AGT GCT

                    145                 150                 155                 160
Leu Thr Thr Ala Ile Pro Leu Phe Thr Val Gln Asn Tyr Gln Val Pro Leu Leu Ser Val
CTT ACA ACC GCT ATT CCT CTT TTT ACA GTT CAA AAT TAT CAA GTA CCT CTT CTA TCA GTA

                    165                 170                 175                 180
Tyr Val Gln Ala Ala Asn Leu His Leu Ser Val Leu Arg Asp Val Ser Val Phe Gly Gln
TAT GTT CAA GCT GCA AAT TTA CAT TTA TCG GTT TTG AGA GAT GTT TCA GTG TTT GGA CAA

                    185                 190                 195                 200
Arg Trp Gly Phe Asp Val Ala Thr Ile Asn Ser Arg Tyr Asn Asp Leu Thr Arg Leu Ile
CGT TGG GGA TTT GAT GTA GCA ACA ATC AAT AGT CGT TAT AAT GAT TTA ACT AGG CTT ATT
```

Figure 4B

```
                205                     210                     215                     220
Gly Thr Tyr Thr Asp Tyr Ala Val Arg Trp Tyr Asn Thr Gly Leu Glu Arg Val Trp Gly
GGC ACC TAT ACA GAT TAT GCT GTA CGC TGG TAT AAT ACG GGA TTA GAA CGT GTA TGG GGA

                225                     230                     235                     240
Pro Asp Ser Arg Asp Trp Val Arg Tyr Asn Gln Phe Arg Arg Glu Leu Thr Leu Thr Val
CCG GAT TCT AGA GAT TGG GTA AGG TAT AAT CAA TTT AGA AGA GAG CTA ACA CTA ACT GTA

                245                     250                     255                     260
Leu Asp Ile Val Ser Leu Phe Pro Asn Tyr Asp Ser Arg Thr Tyr Pro Ile Arg Thr Val
TTA GAT ATC GTT TCT CTG TTC CCG AAC TAT GAT AGT AGA ACG TAT CCA ATT CGA ACA GTT

                265                     270                     275                     280
Ser Gln Leu Thr Arg Glu Ile Tyr Thr Asn Pro Val Leu Glu Asn Phe Asp Gly Ser Phe
TCC CAA TTA ACT AGA GAA ATT TAT ACA AAC CCA GTA TTA GAA AAT TTT GAT GGT AGT TTT

                285                     290                     295                     300
Arg Gly Met Ala Gln Arg Ile Glu Gln Asn Ile Arg Gln Pro His Leu Met Asp Leu Leu
CGT GGA ATG GCT CAG AGA ATA GAA CAG AAT ATT AGG CAA CCA CAT CTT ATG GAT CTC CTT
```

Figure 4C

```
                    305                 310                 315                 320
Asn Ser Ile Thr Ile Tyr Thr Asp Val His Arg Gly Phe Asn Tyr Trp Ser Gly His Gln
AAT AGT ATA ACC ATT TAT ACT GAT GTG CAT AGA GGC TTT AAT TAT TGG TCA GGA CAT CAA

                    325                 330                 335                 340
Ile Thr Ala Ser Pro Val Gly Phe Ala Gly Pro Glu Phe Thr Phe Pro Arg Tyr Gly Thr
ATA ACA GCT TCT CCT GTC GGT TTT GCG GGG CCA GAA TTT ACT TTT CCT AGA TAT GGA ACC

                    345                 350                 355                 360
Met Gly Asn Ala Ala Pro Pro Val Leu Ile Ser Thr Thr Gly Leu Gly Ile Phe Arg Thr
ATG GGA AAT GCT GCT CCA CCC GTA CTG ATC TCA ACT ACT GGT TTG GGG ATT TTT AGA ACA

                    365                 370                 375                 380
Leu Ser Ser Pro Leu Tyr Arg Arg Ile Ile Leu Gly Ser Gly Pro Asn Asn Gln Asn Leu
TTA TCT TCA CCT CTT TAC AGA AGA ATT ATA CTT GGT TCA GGC CCA AAT AAT CAG AAC CTG

                    385                 390                 395                 400
Phe Val Leu Asp Gly Thr Glu Phe Ser Phe Ala Ser Leu Thr Ala Asp Leu Pro Ser Thr
TTT GTC CTT GAT GGA ACG GAA TTT TCT TTT GCC TCC CTA ACA GCC GAT TTA CCT TCT ACT
```

Figure 4D

```
                405                 410                 415                 420
Ile Tyr Arg Gln Arg Gly Thr Val Asp Ser Leu Asp Val Ile Pro Pro Gln Asp Asn Ser
ATA TAC AGA CAA AGG GGA ACG GTC GAT TCA CTA GAT GTA ATA CCG CCA CAG GAT AAT AGT

                425                 430                 435                 440
Val Pro Ala Arg Ala Gly Phe Ser His Arg Leu Ser His Val Thr Met Leu Ser Gln Ala
GTG CCA GCA CGT GCG GGA TTT AGT CAT CGA TTA AGT CAT GTT ACA ATG CTG AGC CAA GCA

                445                 450                 455                 460
Ala Gly Ala Val Tyr Thr Leu Arg Ala Pro Thr Phe Ser Trp Arg His Arg Ser Ala Glu
GCT GGA GCA GTT TAC ACC TTG AGA GCT CCA ACG TTT TCT TGG CGA CAT CGT AGT GCT GAA

                465                 470                 475                 480
Phe Ser Asn Leu Ile Pro Ser Ser Gln Ile Thr Gln Ile Pro Leu Thr Lys Ser Ile Asn
TTC TCT AAC CTA ATT CCT TCA TCA CAA ATC ACA CAG ATA CCT TTA ACA AAG TCT ATT AAT

                485                 490                 495                 500
Leu Gly Ser Gly Thr Ser Val Val Lys Gly Pro Gly Phe Thr Gly Gly Asp Ile Leu Arg
CTT GGC TCT GGG ACC TCT GTT GTT AAA GGA CCA GGA TTT ACA GGA GGA GAT ATT CTT CGA
```

Figure 4E

```
                505                 510                 515                 520
Arg Thr Ser Pro Gly Gln Ile Ser Thr Leu Arg Val Thr Ile Thr Ala Pro Leu Ser Gln
AGA ACT TCA CCT GGC CAG ATT TCA ACC TTA AGA GTG ACT ATT ACT GCA CCA TTA TCA CAA

                525                 530                 535                 540
Arg Tyr Arg Val Arg Ile Arg Tyr Ala Ser Thr Thr Asn Leu Gln Phe His Thr Ser Ile
AGA TAT CGC GTA AGA ATT CGC TAC GCT TCT ACT ACA AAT TTA CAA TTC CAT ACA TCA ATT

                545                 550                 555                 560
Asp Gly Arg Pro Ile Asn Gln Gly Asn Phe Ser Ala Thr Met Ser Ser Gly Gly Asn Leu
GAC GGA AGA CCT ATT AAT CAG GGG AAT TTT TCA GCA ACT ATG AGT AGT GGG GGT AAT TTA

                565                 570                 575                 580
Gln Ser Gly Ser Phe Arg Thr Ala Gly Phe Thr Thr Pro Phe Asn Phe Ser Asn Gly Ser
CAG TCC GGA AGC TTT AGG ACT GCA GGT TTT ACT ACT CCG TTT AAC TTT TCA AAT GGA TCA
                585                 590                 595                 600
Ser Ile Phe Thr Leu Ser Ala His Val Phe Asn Ser Gly Asn Glu Val Tyr Ile Asp Arg
AGT ATA TTT ACG TTA AGT GCT CAT GTC TTC AAT TCA GGC AAT GAA GTT TAT ATA GAT CGA
```

Figure 4F

```
                    605                 610                 615                 620
Ile Glu Phe Val Pro Ala Glu Val Thr Phe Glu Ala Glu Tyr Asp Leu Glu Arg Ala Gln
ATT GAA TTT GTT CCG GCA GAA GTA ACA TTT GAG GCG GAA TAT GAT TTA GAA AGA GCG CAA

                    625                 630                 635                 640
Glu Ala Val Asn Ala Leu Phe Thr Ser Ser Asn Gln Leu Gly Leu Lys Thr Asn Val Thr
GAG GCG GTG AAT GCT CTG TTT ACT TCT TCC AAT CAA CTA GGA TTA AAA ACA AAT GTG ACG

                    645                 650                 655                 660
Asp Tyr His Ile Asp Gln Val Ser Asn Leu Val Glu Cys Leu Ser Gly Glu Phe Cys Leu
GAC TAT CAT ATT GAT CAA GTG TCC AAT CTA GTC GAA TGT TTA TCC GGT GAA TTC TGT CTG

                    665                 670                 675                 680
Asp Glu Lys Arg Glu Leu Ser Glu Lys Val Lys His Ala Lys Arg Leu Ser Asp Glu Arg
GAT GAA AAG AGA GAA TTG TCC GAG AAA GTC AAA CAT GCG AAG CGA CTC AGT GAT GAG CGG

                    685                 690                 695                 700
Asn Leu Leu Gln Asp Pro Asn Phe Arg Gly Ile Asn Arg Gln Pro Asp Arg Gly Trp Arg
AAT TTA CTT CAA GAC CCA AAC TTC AGA GGC ATC AAT AGA CAA CCA GAC CGT GGC TGG AGA
```

Figure 4G

```
                    705                 710                 715                 720
Gly Ser Thr Asp Ile Thr Ile Gln Gly Gly Asp Asp Val Phe Lys Glu Asn Tyr Val Thr
GGC AGT ACG GAT ATT ACC ATC CAA GGA GGA GAT GAC GTA TTC AAA GAG AAT TAC GTC ACA

                    725                 730                 735                 740
Leu Pro Gly Thr Phe Asn Glu Cys Tyr Pro Thr Tyr Leu Tyr Gln Lys Ile Asp Glu Ser
CTA CCG GGT ACC TTT AAT GAG TGT TAT CCT ACG TAT CTG TAT CAA AAA ATA GAT GAG TCG

                    745                 750                 755                 760
Lys Leu Lys Ala Tyr Thr Arg Tyr Gln Leu Arg Gly Tyr Ile Glu Asp Ser Gln Asp Leu
AAA TTA AAA GCC TAT ACC CGT TAC CAA TTA AGA GGG TAC ATC GAG GAT AGT CAA GAC TTA

                    765                 770                 775                 780
Glu Ile Tyr Leu Ile Arg Tyr Asn Thr Lys His Glu Thr Val Asn Val Pro Gly Thr Gly
GAA ATC TAT TTA ATT CGC TAC AAT ACA AAA CAC GAA ACA GTA AAT GTG CCA GGT ACG GGT

                    785                 790                 795                 800
Ser Leu Trp Pro Leu Ser Val Glu Asn Pro Ile Gly Lys Cys Gly Glu Pro Asn Arg Cys
TCC TTA TGG CCG CTT TCA GTC GAA AAT CCA ATT GGA AAG TGC GGA GAA CCA AAT CGA TGC
```

Figure 4H

```
                    805                 810                 815                 820
Ala Pro Gln Leu Glu Trp Asn Pro Asp Leu Asp Cys Ser Cys Arg Asp Gly Glu Lys Cys
GCA CCA CAA CTT GAA TGG AAT CCT GAT CTA GAT TGT TCC TGC AGA GAC GGG GAA AAA TGT

                    825                 830                 835                 840
Ala His His Ser His His Phe Ser Leu Asp Ile Asp Ile Gly Cys Thr Asp Leu Asn Glu
GCA CAT CAC TCC CAT CAT TTC TCC TTG GAC ATT GAT ATT GGA TGT ACA GAT TTA AAT GAG

                    845                 850                 855                 860
Asn Leu Gly Val Trp Val Ile Phe Lys Ile Lys Thr Gln Asp Gly His Ala Arg Leu Gly
AAC TTA GGT GTA TGG GTG ATA TTC AAA ATT AAG ACG CAA GAT GGT CAC GCA AGA CTA GGT

                    865                 870                 875                 880
Asn Leu Glu Phe Leu Glu Glu Lys Pro Leu Val Gly Glu Ser Leu Ala Arg Val Lys Arg
AAT CTA GAG TTT CTC GAA GAG AAA CCA TTA GTA GGC GAA TCG TTA GCA CGC GTG AAG AGA

                    885                 890                 895                 900
Ala Glu Lys Lys Trp Arg Asp Lys Arg Glu Lys Leu Gln Val Glu Thr Asn Ile Val Tyr
GCG GAG AAG AAG TGG AGA GAC AAA CGA GAG AAA TTG CAA GTG GAA ACA AAT ATC GTT TAT
```

Figure 4I

```
                905                 910                 915                 920
Lys Glu Ala Lys Glu Ser Val Asp Ala Leu Phe Val Asn Ser Gln Tyr Asp Arg Leu Gln
AAA GAG GCA AAA GAA TCT GTA GAT GCT TTA TTT GTG AAC TCT CAA TAT GAT AGA TTA CAA

                925                 930                 935                 940
Ala Asp Thr Asp Ile Ala Met Ile His Ala Ala Asp Lys Arg Val His Arg Ile Arg Glu
GCG GAT ACC GAC ATC GCG ATG ATT CAT GCG GCA GAT AAA CGC GTT CAT CGA ATT CGA GAA

                945                 950                 955                 960
Ala Tyr Leu Pro Glu Leu Ser Val Ile Pro Gly Val Asn Ala Gly Ile Phe Glu Glu Leu
GCA TAT CTT CCA GAG TTA TCT GTA ATT CCG GGT GTC AAT GCG GGC ATT TTT GAA GAA TTA

                965                 970                 975                 980
Glu Gly Arg Ile Phe Thr Ala Tyr Ser Leu Tyr Asp Ala Arg Asn Val Ile Lys Asn Gly
GAG GGA CGT ATT TTC ACA GCC TAC TCT TTA TAT GAT GCG AGA AAT GTC ATT AAA AAT GGC

                985                 990                 995                1000
Asp Phe Asn Asn Gly Leu Ser Cys Trp Asn Val Lys Gly His Val Asp Val Glu Glu Gln
GAT TTC AAT AAT GGC TTA TCA TGC TGG AAC GTG AAA GGG CAT GTA GAT GTA GAA GAA CAA
```

Figure 4J

```
                1005                1010                1015                1020
Asn Asn His Arg Ser Val Leu Val Val Pro Glu Trp Glu Ala Glu Val Ser Gln Glu Val
AAC AAC CAC CGT TCG GTT CTT GTT GTC CCG GAA TGG GAA GCA GAG GTG TCA CAA GAG GTT

                1025                1030                1035                1040
Arg Val Cys Pro Gly Arg Gly Tyr Ile Leu Arg Val Thr Ala Tyr Lys Glu Gly Tyr Gly
CGT GTC TGT CCA GGT CGT GGC TAT ATC CTA CGT GTT ACA GCG TAC AAA GAG GGA TAT GGA

                1045                1050                1055                1060
Glu Gly Cys Val Thr Ile His Glu Ile Glu Asp Asn Thr Asp Glu Leu Lys Phe Ser Asn
GAA GGT TGC GTA ACG ATT CAT GAG ATC GAA GAC AAT ACA GAC GAA CTG AAA TTC AGC AAC

                1065                1070                1075                1080
Cys Val Glu Glu Glu Val Tyr Pro Asn Asn Thr Val Thr Cys Asn Asp Tyr Thr Ala Asn
TGT GTA GAA GAG GAA GTA TAT CCA AAC AAC ACG GTA ACG TGT AAT GAT TAT ACT GCA AAT

                1085                1090                1095                1100
Gln Glu Glu Tyr Gly Gly Ala Tyr Thr Ser Arg Asn Arg Gly Tyr Gly Glu Ser Tyr Glu
CAA GAA GAA TAC GGG GGT GCG TAC ACT TCT CGT AAT CGT GGA TAT GGT GAA TCT TAT GAA
```

Figure 4K

```
                    1105                1110                1115                1120
Ser Asn Ser Ser Ile Pro Ala Glu Tyr Ala Pro Val Tyr Glu Glu Ala Tyr Ile Asp Gly
AGT AAT TCT TCC ATA CCA GCT GAG TAT GCG CCA GTT TAT GAG GAA GCA TAT ATA GAT GGA

                    1125                1130                1135                1140
Arg Lys Glu Asn Pro Cys Glu Ser Asn Arg Gly Tyr Gly Asp Tyr Thr Pro Leu Pro Ala
AGA AAA GAG AAT CCT TGT GAA TCT AAC AGA GGA TAT GGG GAT TAC ACG CCA CTA CCA GCT

                    1145                1150                1155                1160
Gly Tyr Val Thr Lys Glu Leu Glu Tyr Phe Pro Glu Thr Asp Lys Val Trp Ile Glu Ile
GGT TAT GTG ACA AAA GAA TTA GAG TAC TTC CCA GAA ACC GAT AAG GTA TGG ATT GAG ATC

                    1165                1170                1175
Gly Glu Thr Glu Gly Thr Phe Ile Val Asp Ser Val Glu Leu Leu Leu Met Glu Glu
GGG GAA ACG GAA GGA ACA TTC ATC GTG GAT AGC GTG GAA TTA CTC CTT ATG GAG GAA
```

Figure 4L

```
               10         20         30         40         50         60
  1 ATGGAAATAA ATAATCAAAA CCAATGTGTG CCTTACAATT GTTTAAGTAA TCCTAAGGAG
 61 ATAATATTAG GCGAGGAAAG GCTAGAAACA GGGAATACTG TAGCAGACAT TTCATTAGGG
121 CTTATTAATT TTCTATATTC TAATTTTGTA CCAGGAGGAG GATTTATAGT AGGTTTACTA
181 GAATTAATAT GGGGATTTAT AGGGCCTTCG CAATGGGATA TTTTTTTAGC TCAAATTGAG
241 CAATTGATTA GTCAAAGAAT AGAAGAATTT GCTAGGAATC AGGCAATTTC AAGATTGGAG

              310        320        330        340        350        360
301 GGGCTAAGCA ATCTTTATAA GGTCTATGTT AGAGCGTTTA GCGACTGGGA GAAAGATCCT
361 ACTAATCCTG CTTTAAGGGA AGAAATGCGT ATACAATTTA ATGACATGAA TAGTGCTCTC
421 ATAACGGCTA TTCCACTTTT TAGAGTTCAA AATTATGAAG TTGCTCTTTT ATCTGTATAT
481 GTTCAAGCCG CAAACTTACA TTTATCTATT TTAAGGGATG TTTCAGTTTT CGGAGAAAGA
541 TGGGGATATG ATACAGCGAC TATCAATAAT CGCTATAGTG ATCTGACTAG CCTTATTCAT

              610        620        630        640        650        660
601 GTTTATACTA ACCATTGTGT GGATACGTAT AATCAGGGAT TAAGGCGTTT GGAAGGTCGT
661 TTTCTTAGCG ATTGGATTGT ATATAATCGT TTCCGGAGAC AATTGACAAT TTCAGTATTA
721 GATATTGTTG CGTTTTTTCC AAATTATGAT ATTAGAACAT ATCCAATTCA AACAGCTACT
781 CAGCTAACGA GGGAAGTCTA TCTGGATTTA CCTTTTATTA ATGAAAATCT TTCTCCTGCA
841 GCAAGCTATC CAACCTTTTC AGCTGCTGAA AGTGCTATAA TTAGAAGTCC TCATTTAGTA
```

Figure 5A

```
           910        920        930        940        950        960
 901 GACTTTTTAA ATAGCTTTAC CATTTATACA GATAGTCTGG CACGTTATGC ATATTGGGGA
 961 GGGCACTTGG TAAATTCTTT CCGCACAGGA ACCACTACTA ATTTGATAAG ATCCCCTTTA
1021 TATGGAAGGG AAGGAAATAC AGAGCGCCCC GTAACTATTA CCGCATCACC TAGCGTACCA
1081 ATATTTAGAA CACTTTCATA TATTACAGGC CTTGACAATT CAAATCCTGT AGCTGGAATC
1141 GAGGGAGTGG AATTCCAAAA TACTATAAGT AGAAGTATCT ATCGTAAAAG CGGTCCAATA

          1210       1220       1230       1240       1250       1260
1201 GATTCTTTTA GTGAATTACC ACCTCAAGAT GCCAGCGTAT CTCCTGCAAT TGGGTATAGT
1261 CACCGTTTAT GCCATGCAAC ATTTTTAGAA CGGATTAGTG GACCAAGAAT AGCAGGCACC
1321 GTATTTTCTT GGACACACCG TAGTGCCAGC CCTACTAATG AAGTAAGTCC ATCTAGAATT
1381 ACACAAATTC CATGGGTAAA GGCGCATACT CTTGCATCTG GTGCCTCCGT CATTAAAGGT
1441 CCTGGATTTA CAGGTGGAGA TATTCTGACT AGGAATAGTA TGGGCGAGCT GGGGACCTTA

          1510       1520       1530       1540       1550       1560
1501 CGAGTAACCT TCACAGGAAG ATTACCACAA AGTTATTATA TACGTTTCCG TTATGCTTCG
1561 GTAGCAAATA GGAGTGGTAC ATTTAGATAT TCACAGCCAC CTTCGTATGG AATTTCATTT
1621 CCAAAAACTA TGGACGCAGG TGAACCACTA ACATCTCGTT CGTTCGCTCA TACAACACTC
1681 TTCACTCCAA TAACCTTTTC ACGAGCTCAA GAAGAATTTG ATCTATACAT CCAATCGGGT
1741 GTTTATATAG ATCGAATTGA ATTTATACCG GTTACTGCAA CATTTGAGGC AGAATATGAT
```

Figure 5B

```
              1810       1820       1830       1840       1850       1860
1801  TTAGAAAGAG CGCAAAAGGT GGTGAATGCC CTGTTTACGT CTACAAACCA ACTAGGGCTA
1861  AAAACAGATG TGACGGATTA TCATATTGAT CAGGTATCCA ATCTAGTTGC GTGTTTATCG
1921  GATGAATTTT GTCTGGATGA AAAGAGAGAA TTGTCCGAGA AAGTTAAACA TGCAAAGCGA
1981  CTCAGTGATG AGCGGAATTT ACTTCAAGAT CCAAACTTCA GAGGGATCAA TAGGCAACCA
2041  GACCGTGGCT GGAGAGGAAG TACGGATATT ACTATCCAAG GAGGAGATGA CGTATTCAAA

              2110       2120       2130       2140       2150       2160
2101  GAGAATTACG TTACGCTACC GGGTACCTTT GATGAGTGCT ATCCAACGTA TTTATATCAA
2161  AAAATAGATG AGTCGAAATT AAAAGCCTAT ACCCGTTATC AATTAAGAGG GTATATCGAA
2221  GATAGTCAAG ACTTAGAAAT CTATTTAATT CGTTACAATG CAAAACACGA AATAGTAAAT
2281  GTACCAGGTA CAGGAAGTTT ATGGCCTCTT TCTGTAGAAA ATCAAATTGG ACCTTGTGGA
2341  GAACCGAATC GATGCGCGCC ACACCTTGAA TGGAATCCTG ATTTACACTG TTCCTGCAGA

              2410       2420       2430       2440       2450       2460
2401  GACGGGGAAA AATGTGCACA TCATTCTCAT CATTTCTCTT TGGACATTGA TGTTGGATGT
2461  ACAGACTTAA ATGAGGACTT AGGTGTATGG GTGATATTCA AGATTAAGAC GCAAGATGGC
2521  CACGCACGAC TAGGGAATCT AGAGTTTCTC GAAGAGAAAC CATTATTAGG AGAAGCACTA
2581  GCTCGTGTGA AAAGAGCGGA GAAAAAATGG AGAGACAAAC GCGAAACATT ACAATTGGAA
2641  ACAACTATCG TTTATAAAGA GGCAAAAGAA TCTGTAGATG CTTTATTTGT AAACTCTCAA
```

Figure 5C

```
                 2710       2720       2730       2740       2750       2760
2701 TATGATAGAT TACAAGCGGA TACGAACATC GCGATGATTC ATGCGGCAGA TAAACGCGTT
2761 CATAGAATTC GAGAAGCGTA TCTGCCGGAG CTGTCTGTGA TTCCGGGTGT CAATGCGGCT
2821 ATTTTTGAAG AATTAGAAGA GCGTATTTTC ACTGCATTTT CCCTATATGA TGCGAGAAAT
2881 ATTATTAAAA ATGGCGATTT CAATAATGGC TTATTATGCT GGAACGTGAA AGGGCATGTA
2941 GAGGTAGAAG AACAAAACAA TCACCGTTCA GTCCTGGTTA TCCCAGAATG GGAGGCAGAA

                 3010       3020       3030       3040       3050       3060
3001 GTGTCACAAG AGGTTCGTGT CTGTCCAGGT CGTGGCTATA TCCTTCGTGT TACAGCGTAC
3061 AAAGAGGGAT ATGGAGAAGG TTGCGTAACG ATCCATGAGA TCGAGAACAA TACAGACGAA
3121 CTGAAATTCA ACAACTGTGT AGAAGAGGAA GTATATCCAA ACAACACGGT AACGTGTATT
3181 AATTATACTG CGACTCAAGA AGAATATGAG GGTACGTACA CTTCTCGTAA TCGAGGATAT
3241 GACGAAGCCT ATGGTAATAA CCCTTCCGTA CCAGCTGATT ATGCGTCAGT CTATGAAGAA

                 3310       3320       3330       3340       3350       3360
3301 AAATCGTATA CAGATAGACG AAGAGAGAAT CCTTGTGAAT CTAACAGAGG ATATGGAGAT
3361 TACACACCAC TACCAGCTGG TTATGTAACA AAGGAATTAG AGTACTTCCC AGAGACCGAT
3421 AAGGTATGGA TTGAGATTGG AGAAACAGAA GGAACATTCA TCGTGGACAG CGTGGAATTA
3481 CTCCTTATGG AGGAA*
```

Segment 140-3634

Figure 5D

```
                                5                                     10                                    15
  1 Met Glu Ile Asn Asn Gln Asn Gln Cys Val Pro Tyr Asn Cys Leu
 16 Ser Asn Pro Lys Glu Ile Ile Leu Gly Glu Glu Arg Leu Glu Thr
 31 Gly Asn Thr Val Ala Asp Ile Ser Leu Gly Leu Ile Asn Phe Leu
 46 Tyr Ser Asn Phe Val Pro Gly Gly Gly Phe Ile Val Gly Leu Leu
 61 Glu Leu Ile Trp Gly Phe Ile Gly Pro Ser Gln Trp Asp Ile Phe
 76 Leu Ala Gln Ile Glu Gln Leu Ile Ser Gln Arg Ile Glu Glu Phe
 91 Ala Arg Asn Gln Ala Ile Ser Arg Leu Glu Gly Leu Ser Asn Leu
106 Tyr Lys Val Tyr Val Arg Ala Phe Ser Asp Trp Glu Lys Asp Pro
121 Thr Asn Pro Ala Leu Arg Glu Glu Met Arg Ile Gln Phe Asn Asp
136 Met Asn Ser Ala Leu Ile Thr Ala Ile Pro Leu Phe Arg Val Gln
151 Asn Tyr Glu Val Ala Leu Leu Ser Val Tyr Val Gln Ala Ala Asn
166 Leu His Leu Ser Ile Leu Arg Asp Val Ser Val Phe Gly Glu Arg
181 Trp Gly Tyr Asp Thr Ala Thr Ile Asn Asn Arg Tyr Ser Asp Leu
196 Thr Ser Leu Ile His Val Tyr Thr Asn His Cys Val Asp Thr Tyr
211 Asn Gln Gly Leu Arg Arg Leu Glu Gly Arg Phe Leu Ser Asp Trp
```

Figure 6A

```
226 Ile Val Tyr Asn Arg Phe Arg Arg Gln Leu Thr Ile Ser Val Leu
241 Asp Ile Val Ala Phe Phe Pro Asn Tyr Asp Ile Arg Thr Tyr Pro
256 Ile Gln Thr Ala Thr Gln Leu Thr Arg Glu Val Tyr Leu Asp Leu
271 Pro Phe Ile Asn Glu Asn Leu Ser Pro Ala Ala Ser Tyr Pro Thr
286 Phe Ser Ala Ala Glu Ser Ala Ile Ile Arg Ser Pro His Leu Val
301 Asp Phe Leu Asn Ser Phe Thr Ile Tyr Thr Asp Ser Leu Ala Arg
316 Tyr Ala Tyr Trp Gly Gly His Leu Val Asn Ser Phe Arg Thr Gly
331 Thr Thr Thr Asn Leu Ile Arg Ser Pro Leu Tyr Gly Arg Glu Gly
346 Asn Thr Glu Arg Pro Val Thr Ile Thr Ala Ser Pro Ser Val Pro
361 Ile Phe Arg Thr Leu Ser Tyr Ile Thr Gly Leu Asp Asn Ser Asn
376 Pro Val Ala Gly Ile Glu Gly Val Glu Phe Gln Asn Thr Ile Ser
391 Arg Ser Ile Tyr Arg Lys Ser Gly Pro Ile Asp Ser Phe Ser Glu
406 Leu Pro Pro Gln Asp Ala Ser Val Ser Pro Ala Ile Gly Tyr Ser
421 His Arg Leu Cys His Ala Thr Phe Leu Glu Arg Ile Ser Gly Pro
436 Arg Ile Ala Gly Thr Val Phe Ser Trp Thr His Arg Ser Ala Ser
```

Figure 6B

```
451 Pro Thr Asn Glu Val Ser Pro Ser Arg Ile Thr Gln Ile Pro Trp
466 Val Lys Ala His Thr Leu Ala Ser Gly Ala Ser Val Ile Lys Gly
481 Pro Gly Phe Thr Gly Gly Asp Ile Leu Thr Arg Asn Ser Met Gly
496 Glu Leu Gly Thr Leu Arg Val Thr Phe Thr Gly Arg Leu Pro Gln
511 Ser Tyr Tyr Ile Arg Phe Arg Tyr Ala Ser Val Ala Asn Arg Ser
526 Gly Thr Phe Arg Tyr Ser Gln Pro Pro Ser Tyr Gly Ile Ser Phe
541 Pro Lys Thr Met Asp Ala Gly Glu Pro Leu Thr Ser Arg Ser Phe
556 Ala His Thr Thr Leu Phe Thr Pro Ile Thr Phe Ser Arg Ala Gln
571 Glu Glu Phe Asp Leu Tyr Ile Gln Ser Gly Val Tyr Ile Asp Arg
586 Ile Glu Phe Ile Pro Val Thr Ala Thr Phe Glu Ala Glu Tyr Asp
601 Leu Glu Arg Ala Gln Lys Val Val Asn Ala Leu Phe Thr Ser Thr
616 Asn Gln Leu Gly Leu Lys Thr Asp Val Thr Asp Tyr His Ile Asp
631 Gln Val Ser Asn Leu Val Ala Cys Leu Ser Asp Glu Phe Cys Leu
646 Asp Glu Lys Arg Glu Leu Ser Glu Lys Val Lys His Ala Lys Arg
661 Leu Ser Asp Glu Arg Asn Leu Leu Gln Asp Pro Asn Phe Arg Gly
```

Figure 6C

```
676 Ile Asn Arg Gln Pro Asp Arg Gly Trp Arg Gly Ser Thr Asp Ile
691 Thr Ile Gln Gly Gly Asp Asp Val Phe Lys Glu Asn Tyr Val Thr
706 Leu Pro Gly Thr Phe Asp Glu Cys Tyr Pro Thr Tyr Leu Tyr Gln
721 Lys Ile Asp Glu Ser Lys Leu Lys Ala Tyr Thr Arg Tyr Gln Leu
736 Arg Gly Tyr Ile Glu Asp Ser Gln Asp Leu Glu Ile Tyr Leu Ile
751 Arg Tyr Asn Ala Lys His Glu Ile Val Asn Val Pro Gly Thr Gly
766 Ser Leu Trp Pro Leu Ser Val Glu Asn Gln Ile Gly Pro Cys Gly
781 Glu Pro Asn Arg Cys Ala Pro His Leu Glu Trp Asn Pro Asp Leu
796 His Cys Ser Cys Arg Asp Gly Glu Lys Cys Ala His His Ser His
811 His Phe Ser Leu Asp Ile Asp Val Gly Cys Thr Asp Leu Asn Glu
826 Asp Leu Gly Val Trp Val Ile Phe Lys Ile Lys Thr Gln Asp Gly
841 His Ala Arg Leu Gly Asn Leu Glu Phe Leu Glu Glu Lys Pro Leu
856 Leu Gly Glu Ala Leu Ala Arg Val Lys Arg Ala Glu Lys Lys Trp
871 Arg Asp Lys Arg Glu Thr Leu Gln Leu Glu Thr Thr Ile Val Tyr
886 Lys Glu Ala Lys Glu Ser Val Asp Ala Leu Phe Val Asn Ser Gln
```

Figure 6D

```
 901 Tyr Asp Arg Leu Gln Ala Asp Thr Asn Ile Ala Met Ile His Ala
 916 Ala Asp Lys Arg Val His Arg Ile Arg Glu Ala Tyr Leu Pro Glu
 931 Leu Ser Val Ile Pro Gly Val Asn Ala Ala Ile Phe Glu Glu Leu
 946 Glu Glu Arg Ile Phe Thr Ala Phe Ser Leu Tyr Asp Ala Arg Asn
 961 Ile Ile Lys Asn Gly Asp Phe Asn Asn Gly Leu Leu Cys Trp Asn
 976 Val Lys Gly His Val Glu Val Glu Glu Gln Asn Asn His Arg Ser
 991 Val Leu Val Ile Pro Glu Trp Glu Ala Glu Val Ser Gln Glu Val
1006 Arg Val Cys Pro Gly Arg Gly Tyr Ile Leu Arg Val Thr Ala Tyr
1021 Lys Glu Gly Tyr Gly Glu Gly Cys Val Thr Ile His Glu Ile Glu
1036 Asn Asn Thr Asp Glu Leu Lys Phe Asn Asn Cys Val Glu Glu Glu
1051 Val Tyr Pro Asn Asn Thr Val Thr Cys Ile Asn Tyr Thr Ala Thr
1066 Gln Glu Glu Tyr Glu Gly Thr Tyr Thr Ser Arg Asn Arg Gly Tyr
1081 Asp Glu Ala Tyr Gly Asn Asn Pro Ser Val Pro Ala Asp Tyr Ala
1096 Ser Val Tyr Glu Glu Lys Ser Tyr Thr Asp Arg Arg Arg Glu Asn
1111 Pro Cys Glu Ser Asn Arg Gly Tyr Gly Asp Tyr Thr Pro Leu Pro
1126 Ala Gly Tyr Val Thr Lys Glu Leu Glu Tyr Phe Pro Glu Thr Asp
1141 Lys Val Trp Ile Glu Ile Gly Glu Thr Glu Gly Thr Phe Ile Val
1156 Asp Ser Val Glu Leu Leu Leu Met Glu Glu
```

Fragment 1-*

Figure 6E

```
                    5                                 10                                 15                                 20
Met Glu Ile Asn Asn Gln Asn Gln Cys Val Pro Tyr Asn Cys Leu Ser Asn Pro Lys Glu
ATG GAA ATA AAT AAT CAA AAC CAA TGT GTG CCT TAC AAT TGT TTA AGT AAT CCT AAG GAG

                   25                                 30                                 35                                 40
Ile Ile Leu Gly Glu Glu Arg Leu Glu Thr Gly Asn Thr Val Ala Asp Ile Ser Leu Gly
ATA ATA TTA GGC GAG GAA AGG CTA GAA ACA GGG AAT ACT GTA GCA GAC ATT TCA TTA GGG

                   45                                 50                                 55                                 60
Leu Ile Asn Phe Leu Tyr Ser Asn Phe Val Pro Gly Gly Gly Phe Ile Val Gly Leu Leu
CTT ATT AAT TTT CTA TAT TCT AAT TTT GTA CCA GGA GGA GGA TTT ATA GTA GGT TTA CTA

                   65                                 70                                 75                                 80
Glu Leu Ile Trp Gly Phe Ile Gly Pro Ser Gln Trp Asp Ile Phe Leu Ala Gln Ile Glu
GAA TTA ATA TGG GGA TTT ATA GGG CCT TCG CAA TGG GAT ATT TTT TTA GCT CAA ATT GAG

                   85                                 90                                 95                                100
Gln Leu Ile Ser Gln Arg Ile Glu Glu Phe Ala Arg Asn Gln Ala Ile Ser Arg Leu Glu
CAA TTG ATT AGT CAA AGA ATA GAA GAA TTT GCT AGG AAT CAG GCA ATT TCA AGA TTG GAG
```

Figure 7A

```
                    105                      110                      115                      120
Gly Leu Ser Asn Leu Tyr Lys Val Tyr Val Arg Ala Phe Ser Asp Trp Glu Lys Asp Pro
GGG CTA AGC AAT CTT TAT AAG GTC TAT GTT AGA GCG TTT AGC GAC TGG GAG AAA GAT CCT

                    125                      130                      135                      140
Thr Asn Pro Ala Leu Arg Glu Glu Met Arg Ile Gln Phe Asn Asp Met Asn Ser Ala Leu
ACT AAT CCT GCT TTA AGG GAA GAA ATG CGT ATA CAA TTT AAT GAC ATG AAT AGT GCT CTC

                    145                      150                      155                      160
Ile Thr Ala Ile Pro Leu Phe Arg Val Gln Asn Tyr Glu Val Ala Leu Leu Ser Val Tyr
ATA ACG GCT ATT CCA CTT TTT AGA GTT CAA AAT TAT GAA GTT GCT CTT TTA TCT GTA TAT

                    165                      170                      175                      180
Val Gln Ala Ala Asn Leu His Leu Ser Ile Leu Arg Asp Val Ser Val Phe Gly Glu Arg
GTT CAA GCC GCA AAC TTA CAT TTA TCT ATT TTA AGG GAT GTT TCA GTT TTC GGA GAA AGA

                    185                      190                      195                      200
Trp Gly Tyr Asp Thr Ala Thr Ile Asn Asn Arg Tyr Ser Asp Leu Thr Ser Leu Ile His
TGG GGA TAT GAT ACA GCG ACT ATC AAT AAT CGC TAT AGT GAT CTG ACT AGC CTT ATT CAT
```

Figure 7B

```
                    205                 210                 215                 220
Val Tyr Thr Asn His Cys Val Asp Thr Tyr Asn Gln Gly Leu Arg Arg Leu Glu Gly Arg
GTT TAT ACT AAC CAT TGT GTG GAT ACG TAT AAT CAG GGA TTA AGG CGT TTG GAA GGT CGT

                    225                 230                 235                 240
Phe Leu Ser Asp Trp Ile Val Tyr Asn Arg Phe Arg Arg Gln Leu Thr Ile Ser Val Leu
TTT CTT AGC GAT TGG ATT GTA TAT AAT CGT TTC CGG AGA CAA TTG ACA ATT TCA GTA TTA

                    245                 250                 255                 260
Asp Ile Val Ala Phe Phe Pro Asn Tyr Asp Ile Arg Thr Tyr Pro Ile Gln Thr Ala Thr
GAT ATT GTT GCG TTT TTT CCA AAT TAT GAT ATT AGA ACA TAT CCA ATT CAA ACA GCT ACT

                    265                 270                 275                 280
Gln Leu Thr Arg Glu Val Tyr Leu Asp Leu Pro Phe Ile Asn Glu Asn Leu Ser Pro Ala
CAG CTA ACG AGG GAA GTC TAT CTG GAT TTA CCT TTT ATT AAT GAA AAT CTT TCT CCT GCA
                    285                 290                 295                 300
Ala Ser Tyr Pro Thr Phe Ser Ala Ala Glu Ser Ala Ile Ile Arg Ser Pro His Leu Val
GCA AGC TAT CCA ACC TTT TCA GCT GCT GAA AGT GCT ATA ATT AGA AGT CCT CAT TTA GTA
```

Figure 7C

```
                    305                 310                 315                 320
Asp Phe Leu Asn Ser Phe Thr Ile Tyr Thr Asp Ser Leu Ala Arg Tyr Ala Tyr Trp Gly
GAC TTT TTA AAT AGC TTT ACC ATT TAT ACA GAT AGT CTG GCA CGT TAT GCA TAT TGG GGA

                    325                 330                 335                 340
Gly His Leu Val Asn Ser Phe Arg Thr Gly Thr Thr Thr Asn Leu Ile Arg Ser Pro Leu
GGG CAC TTG GTA AAT TCT TTC CGC ACA GGA ACC ACT ACT AAT TTG ATA AGA TCC CCT TTA

                    345                 350                 355                 360
Tyr Gly Arg Glu Gly Asn Thr Glu Arg Pro Val Thr Ile Thr Ala Ser Pro Ser Val Pro
TAT GGA AGG GAA GGA AAT ACA GAG CGC CCC GTA ACT ATT ACC GCA TCA CCT AGC GTA CCA

                    365                 370                 375                 380
Ile Phe Arg Thr Leu Ser Tyr Ile Thr Gly Leu Asp Asn Ser Asn Pro Val Ala Gly Ile
ATA TTT AGA ACA CTT TCA TAT ATT ACA GGC CTT GAC AAT TCA AAT CCT GTA GCT GGA ATC

                    385                 390                 395                 400
Glu Gly Val Glu Phe Gln Asn Thr Ile Ser Arg Ser Ile Tyr Arg Lys Ser Gly Pro Ile
GAG GGA GTG GAA TTC CAA AAT ACT ATA AGT AGA AGT ATC TAT CGT AAA AGC GGT CCA ATA
```

Figure 7D

```
                405                 410                 415                 420
Asp Ser Phe Ser Glu Leu Pro Pro Gln Asp Ala Ser Val Ser Pro Ala Ile Gly Tyr Ser
GAT TCT TTT AGT GAA TTA CCA CCT CAA GAT GCC AGC GTA TCT CCT GCA ATT GGG TAT AGT

                425                 430                 435                 440
His Arg Leu Cys His Ala Thr Phe Leu Glu Arg Ile Ser Gly Pro Arg Ile Ala Gly Thr
CAC CGT TTA TGC CAT GCA ACA TTT TTA GAA CGG ATT AGT GGA CCA AGA ATA GCA GGC ACC

                445                 450                 455                 460
Val Phe Ser Trp Thr His Arg Ser Ala Ser Pro Thr Asn Glu Val Ser Pro Ser Arg Ile
GTA TTT TCT TGG ACA CAC CGT AGT GCC AGC CCT ACT AAT GAA GTA AGT CCA TCT AGA ATT

                465                 470                 475                 480
Thr Gln Ile Pro Trp Val Lys Ala His Thr Leu Ala Ser Gly Ala Ser Val Ile Lys Gly
ACA CAA ATT CCA TGG GTA AAG GCG CAT ACT CTT GCA TCT GGT GCC TCC GTC ATT AAA GGT

                485                 490                 495                 500
Pro Gly Phe Thr Gly Gly Asp Ile Leu Thr Arg Asn Ser Met Gly Glu Leu Gly Thr Leu
CCT GGA TTT ACA GGT GGA GAT ATT CTG ACT AGG AAT AGT ATG GGC GAG CTG GGG ACC TTA
```

Figure 7E

```
                505                 510                 515                 520
Arg Val Thr Phe Thr Gly Arg Leu Pro Gln Ser Tyr Tyr Ile Arg Phe Arg Tyr Ala Ser
CGA GTA ACC TTC ACA GGA AGA TTA CCA CAA AGT TAT TAT ATA CGT TTC CGT TAT GCT TCG

                525                 530                 535                 540
Val Ala Asn Arg Ser Gly Thr Phe Arg Tyr Ser Gln Pro Pro Ser Tyr Gly Ile Ser Phe
GTA GCA AAT AGG AGT GGT ACA TTT AGA TAT TCA CAG CCA CCT TCG TAT GGA ATT TCA TTT

                545                 550                 555                 560
Pro Lys Thr Met Asp Ala Gly Glu Pro Leu Thr Ser Arg Ser Phe Ala His Thr Thr Leu
CCA AAA ACT ATG GAC GCA GGT GAA CCA CTA ACA TCT CGT TCG TTC GCT CAT ACA ACA CTC

                565                 570                 575                 580
Phe Thr Pro Ile Thr Phe Ser Arg Ala Gln Glu Glu Phe Asp Leu Tyr Ile Gln Ser Gly
TTC ACT CCA ATA ACC TTT TCA CGA GCT CAA GAA GAA TTT GAT CTA TAC ATC CAA TCG GGT
                585                 590                 595                 600
Val Tyr Ile Asp Arg Ile Glu Phe Ile Pro Val Thr Ala Thr Phe Glu Ala Glu Tyr Asp
GTT TAT ATA GAT CGA ATT GAA TTT ATA CCG GTT ACT GCA ACA TTT GAG GCA GAA TAT GAT
```

Figure 7F

```
                        605                 610                  615                 620
Leu Glu Arg Ala Gln Lys Val Val Asn Ala Leu Phe Thr Ser Thr Asn Gln Leu Gly Leu
TTA GAA AGA GCG CAA AAG GTG GTG AAT GCC CTG TTT ACG TCT ACA AAC CAA CTA GGG CTA

                        625                 630                  635                 640
Lys Thr Asp Val Thr Asp Tyr His Ile Asp Gln Val Ser Asn Leu Val Ala Cys Leu Ser
AAA ACA GAT GTG ACG GAT TAT CAT ATT GAT CAG GTA TCC AAT CTA GTT GCG TGT TTA TCG

                        645                 650                  655                 660
Asp Glu Phe Cys Leu Asp Glu Lys Arg Glu Leu Ser Glu Lys Val Lys His Ala Lys Arg
GAT GAA TTT TGT CTG GAT GAA AAG AGA GAA TTG TCC GAG AAA GTT AAA CAT GCA AAG CGA

                        665                 670                  675                 680
Leu Ser Asp Glu Arg Asn Leu Leu Gln Asp Pro Asn Phe Arg Gly Ile Asn Arg Gln Pro
CTC AGT GAT GAG CGG AAT TTA CTT CAA GAT CCA AAC TTC AGA GGG ATC AAT AGG CAA CCA

                        685                 690                  695                 700
Asp Arg Gly Trp Arg Gly Ser Thr Asp Ile Thr Ile Gln Gly Gly Asp Asp Val Phe Lys
GAC CGT GGC TGG AGA GGA AGT ACG GAT ATT ACT ATC CAA GGA GGA GAT GAC GTA TTC AAA
```

Figure 7G

```
                    705                 710                 715                 720
Glu Asn Tyr Val Thr Leu Pro Gly Thr Phe Asp Glu Cys Tyr Pro Thr Tyr Leu Tyr Gln
GAG AAT TAC GTT ACG CTA CCG GGT ACC TTT GAT GAG TGC TAT CCA ACG TAT TTA TAT CAA

                    725                 730                 735                 740
Lys Ile Asp Glu Ser Lys Leu Lys Ala Tyr Thr Arg Tyr Gln Leu Arg Gly Tyr Ile Glu
AAA ATA GAT GAG TCG AAA TTA AAA GCC TAT ACC CGT TAT CAA TTA AGA GGG TAT ATC GAA

                    745                 750                 755                 760
Asp Ser Gln Asp Leu Glu Ile Tyr Leu Ile Arg Tyr Asn Ala Lys His Glu Ile Val Asn
GAT AGT CAA GAC TTA GAA ATC TAT TTA ATT CGT TAC AAT GCA AAA CAC GAA ATA GTA AAT

                    765                 770                 775                 780
Val Pro Gly Thr Gly Ser Leu Trp Pro Leu Ser Val Glu Asn Gln Ile Gly Pro Cys Gly
GTA CCA GGT ACA GGA AGT TTA TGG CCT CTT TCT GTA GAA AAT CAA ATT GGA CCT TGT GGA

                    785                 790                 795                 800
Glu Pro Asn Arg Cys Ala Pro His Leu Glu Trp Asn Pro Asp Leu His Cys Ser Cys Arg
GAA CCG AAT CGA TGC GCG CCA CAC CTT GAA TGG AAT CCT GAT TTA CAC TGT TCC TGC AGA
```

Figure 7H

```
                    805                 810                 815                 820
Asp Gly Glu Lys Cys Ala His His Ser His His Phe Ser Leu Asp Ile Asp Val Gly Cys
GAC GGG GAA AAA TGT GCA CAT CAT TCT CAT CAT TTC TCT TTG GAC ATT GAT GTT GGA TGT

                    825                 830                 835                 840
Thr Asp Leu Asn Glu Asp Leu Gly Val Trp Val Ile Phe Lys Ile Lys Thr Gln Asp Gly
ACA GAC TTA AAT GAG GAC TTA GGT GTA TGG GTG ATA TTC AAG ATT AAG ACG CAA GAT GGC

                    845                 850                 855                 860
His Ala Arg Leu Gly Asn Leu Glu Phe Leu Glu Glu Lys Pro Leu Leu Gly Glu Ala Leu
CAC GCA CGA CTA GGG AAT CTA GAG TTT CTC GAA GAG AAA CCA TTA TTA GGA GAA GCA CTA

                    865                 870                 875                 880
Ala Arg Val Lys Arg Ala Glu Lys Lys Trp Arg Asp Lys Arg Glu Thr Leu Gln Leu Glu
GCT CGT GTG AAA AGA GCG GAG AAA AAA TGG AGA GAC AAA CGC GAA ACA TTA CAA TTG GAA
                    885                 890                 895                 900
Thr Thr Ile Val Tyr Lys Glu Ala Lys Glu Ser Val Asp Ala Leu Phe Val Asn Ser Gln
ACA ACT ATC GTT TAT AAA GAG GCA AAA GAA TCT GTA GAT GCT TTA TTT GTA AAC TCT CAA
```

Figure 7I

```
                    905                      910                      915                      920
Tyr Asp Arg Leu Gln Ala Asp Thr Asn Ile Ala Met Ile His Ala Ala Asp Lys Arg Val
TAT GAT AGA TTA CAA GCG GAT ACG AAC ATC GCG ATG ATT CAT GCG GCA GAT AAA CGC GTT

                    925                      930                      935                      940
His Arg Ile Arg Glu Ala Tyr Leu Pro Glu Leu Ser Val Ile Pro Gly Val Asn Ala Ala
CAT AGA ATT CGA GAA GCG TAT CTG CCG GAG CTG TCT GTG ATT CCG GGT GTC AAT GCG GCT

                    945                      950                      955                      960
Ile Phe Glu Glu Leu Glu Glu Arg Ile Phe Thr Ala Phe Ser Leu Tyr Asp Ala Arg Asn
ATT TTT GAA GAA TTA GAA GAG CGT ATT TTC ACT GCA TTT TCC CTA TAT GAT GCG AGA AAT

                    965                      970                      975                      980
Ile Ile Lys Asn Gly Asp Phe Asn Asn Gly Leu Leu Cys Trp Asn Val Lys Gly His Val
ATT ATT AAA AAT GGC GAT TTC AAT AAT GGC TTA TTA TGC TGG AAC GTG AAA GGG CAT GTA

                    985                      990                      995                     1000
Glu Val Glu Glu Gln Asn Asn His Arg Ser Val Leu Val Ile Pro Glu Trp Glu Ala Glu
GAG GTA GAA GAA CAA AAC AAT CAC CGT TCA GTC CTG GTT ATC CCA GAA TGG GAG GCA GAA
```

Figure 7J

```
                    1005                                     1010                                     1015                                     1020
Val Ser Gln Glu Val Arg Val Cys Pro Gly Arg Gly Tyr Ile Leu Arg Val Thr Ala Tyr
GTG TCA CAA GAG GTT CGT GTC TGT CCA GGT CGT GGC TAT ATC CTT CGT GTT ACA GCG TAC

                    1025                                     1030                                     1035                                     1040
Lys Glu Gly Tyr Gly Glu Gly Cys Val Thr Ile His Glu Ile Glu Asn Asn Thr Asp Glu
AAA GAG GGA TAT GGA GAA GGT TGC GTA ACG ATC CAT GAG ATC GAG AAC AAT ACA GAC GAA

                    1045                                     1050                                     1055                                     1060
Leu Lys Phe Asn Asn Cys Val Glu Glu Glu Val Tyr Pro Asn Asn Thr Val Thr Cys Ile
CTG AAA TTC AAC AAC TGT GTA GAA GAG GAA GTA TAT CCA AAC AAC ACG GTA ACG TGT ATT

                    1065                                     1070                                     1075                                     1080
Asn Tyr Thr Ala Thr Gln Glu Glu Tyr Glu Gly Thr Tyr Thr Ser Arg Asn Arg Gly Tyr
AAT TAT ACT GCG ACT CAA GAA GAA TAT GAG GGT ACG TAC ACT TCT CGT AAT CGA GGA TAT

                    1085                                     1090                                     1095                                     1100
Asp Glu Ala Tyr Gly Asn Asn Pro Ser Val Pro Ala Asp Tyr Ala Ser Val Tyr Glu Glu
GAC GAA GCC TAT GGT AAT AAC CCT TCC GTA CCA GCT GAT TAT GCG TCA GTC TAT GAA GAA
```

Figure 7K

```
                        1105                                    1110                                    1115                                    1120
Lys Ser Tyr Thr Asp Arg Arg Arg Glu Asn Pro Cys Glu Ser Asn Arg Gly Tyr Gly Asp
AAA TCG TAT ACA GAT AGA CGA AGA GAG AAT CCT TGT GAA TCT AAC AGA GGA TAT GGA GAT

                        1125                                    1130                                    1135                                    1140
Tyr Thr Pro Leu Pro Ala Gly Tyr Val Thr Lys Glu Leu Glu Tyr Phe Pro Glu Thr Asp
TAC ACA CCA CTA CCA GCT GGT TAT GTA ACA AAG GAA TTA GAG TAC TTC CCA GAG ACC GAT

                        1145                                    1150                                    1155                                    1160
Lys Val Trp Ile Glu Ile Gly Glu Thr Glu Gly Thr Phe Ile Val Asp Ser Val Glu Leu
AAG GTA TGG ATT GAG ATT GGA GAA ACA GAA GGA ACA TTC ATC GTG GAC AGC GTG GAA TTA

                        1165
Leu Leu Met Glu Glu
CTC CTT ATG GAG GAA
```

Figure 7L

```
             10         20         30         40         50         60
  1 ATGGAGGAAA ATAATCAAAA TCAATGCATA CCTTACAATT GTTTAAGTAA TCCTGAAGAA
 61 GTACTTTTGG ATGGAGAACG GATATCAACT GGTAATTCAT CAATTGATAT TTCTCTGTCA
121 CTTGTTCAGT TTCTGGTATC TAACTTTGTA CCAGGGGGAG GATTTTTAGT TGGATTAATA
181 GATTTTGTAT GGGGAATAGT TGGCCCTTCT CAATGGGATG CATTTCTAGT ACAAATTGAA
241 CAATTAATTA ATGAAAGAAT AGCTGAATTT GCTAGGAATG CTGCTATTGC TAATTTAGAA

            310        320        330        340        350        360
301 GGATTAGGAA ACAATTTCAA TATATATGTG GAAGCATTTA AAGAATGGGA AGAAGATCCT
361 AATAATCCAG CAACCAGGAC CAGAGTAATT GATCGCTTTC GTATACTTGA TGGGCTACTT
421 GAAAGGGACA TTCCTTCGTT TCGAATTTCT GGATTTGAAG TACCCCTTTT ATCCGTTTAT
481 GCTCAAGCGG CCAATCTGCA TCTAGCTATA TTAAGAGATT CTGTAATTTT TGGAGAAAGA
541 TGGGGATTGA CAACGATAAA TGTCAATGAA AACTATAATA GACTAATTAG GCATATTGAT

            610        620        630        640        650        660
601 GAATATGCTG ATCACTGTGC AAATACGTAT AATCGGGGAT TAAATAATTT ACCGAAATCT
661 ACGTATCAAG ATTGGATAAC ATATAATCGA TTACGGAGAG ACTTAACATT GACTGTATTA
721 GATATCGCCG CTTTCTTTCC AAACTATGAC AATAGGAGAT ATCCAATTCA GCCAGTTGGT
781 CAACTAACAA GGGAAGTTTA TACGGACCCA TTAATTAATT TTAATCCACA GTTACAGTCT
841 GTAGCTCAAT TACCTACTTT TAACGTTATG GAGAGCAGCG CAATTAGAAA TCCTCATTTA
```

Figure 8A

```
            910        920        930        940        950        960
 901 TTTGATATAT TGAATAATCT TACAATCTTT ACGGATTGGT TTAGTGTTGG ACGCAATTTT
 961 TATTGGGGAG GACATCGAGT AATATCTAGC CTTATAGGAG GTGGTAACAT AACATCTCCT
1021 ATATATGGAA GAGAGGCGAA CCAGGAGCCT CCAAGATCCT TTACTTTTAA TGGACCGGTA
1081 TTTAGGACTT TATCAAATCC TACTTTACGA TTATTACAGC AACCTTGGCC AGCGCCACCA
1141 TTTAATTTAC GTGGTGTTGA AGGAGTAGAA TTTTCTACAC CTACAAATAG CTTTACGTAT

           1210       1220       1230       1240       1250       1260
1201 CGAGGAAGAG GTACGGTTGA TTCTTTAACT GAATTACCGC CTGAGGATAA TAGTGTGCCA
1261 CCTCGCGAAG GATATAGTCA TCGTTTATGT CATGCAACTT TTGTTCAAAG ATCTGGAACA
1321 CCTTTTTTAA CAACTGGTGT AGTATTTTCT TGGACGCATC GTAGTGCAAC TCTTACAAAT
1381 ACAATTGATC CAGAGAGAAT TAATCAAATA CCTTTAGTGA AAGGATTTAG AGTTTGGGGG
1441 GGCACCTCTG TCATTACAGG ACCAGGATTT ACAGGAGGGG ATATCCTTCG AAGAAATACC

           1510       1520       1530       1540       1550       1560
1501 TTTGGTGATT TTGTATCTCT ACAAGTCAAT ATTAATTCAC CAATTACCCA AAGATACCGT
1561 TTAAGATTTC GTTACGCTTC CAGTAGGGAT GCACGAGTTA TAGTATTAAC AGGAGCGGCA
1621 TCCACAGGAG TGGGAGGCCA AGTTAGTGTA AATATGCCTC TTCAGAAAAC TATGGAAATA
1681 GGGGAGAACT TAACATCTAG AACATTTAGA TATACCGATT TTAGTAATCC TTTTTCATTT
1741 AGAGCTAATC CAGATATAAT TGGGATAAGT GAACAACCTC TATTTGGTGC AGGTTCTATT
```

Figure 8B

```
                1810       1820       1830       1840       1850       1860
1801 AGTAGCGGTG AACTTTATAT AGATAAAATT GAAATTATTC TAGCAGATGC AACATTTGAA
1861 GCAGAATCTG ATTTAGAAAG AGCACAAAAG GCGGTGAATG CCCTGTTTAC TTCTTCCAAT
1921 CAAATCGGGT TAAAAACCGA TGTGACGGAT TATCATATTG ATCAAGTATC CAATTTAGTG
1981 GATTGTTTAT CAGATGAATT TTGTCTGGAT GAAAAGCGAG AATTGTCCGA GAAAGTCAAA
2041 CATGCGAAGC GACTCAGTGA TGAGCGGAAT TTACTTCAAG ATCCAAACTT CAGAGGGATC

                2110       2120       2130       2140       2150       2160
2101 AATAGACAAC CAGACCGTGG CTGGAGAGGA AGTACAGATA TTACCATCCA AGGAGGAGAT
2161 GACGTATTCA AAGAGAATTA CGTCACACTA CCGGGTACCG TTGATGAGTG CTATCCAACG
2221 TATTTATATC AGAAAATAGA TGAGTCGAAA TTAAAAGCTT ATACCCGTTA TGAATTAAGA
2281 GGGTATATCG AAGATAGTCA AGACTTAGAA ATCTATTTGA TCCGTTACAA TGCAAAACAC
2341 GAAATAGTAA ATGTGCCAGG CACGGGTTCC TTATGGCCGC TTTCAGCCCA AAGTCCAATC

                2410       2420       2430       2440       2450       2460
2401 GGAAAGTGTG GAGAACCGAA TCGATGCGCG CCACACCTTG AATGGAATCC TGATCTAGAT
2461 TGTTCCTGCA GAGACGGGGA AAAATGTGCA CATCATTCCC ATCATTTCAC CTTGGATATT
2521 GATGTTGGAT GTACAGACTT AAATGAGGAC TTAGGTGTAT GGGTGATATT CAAGATTAAG
2581 ACGCAAGATG GCCATGCAAG ACTAGGGAAT CTAGAGTTTC TCGAAGAGAA ACCATTATTA
2641 GGGGAAGCAC TAGCTCGTGT GAAAAGAGCG GAGAAGAAGT GGAGAGACAA ACGAGAGAAA
```

Figure 8C

```
           2710       2720       2730       2740       2750       2760
2701 CTGCAGTTGG AAACAAATAT TGTTTATAAA GAGGCAAAAG AATCTGTAGA TGCTTTATTT
2761 GTAAACTCTC AATATGATAG ATTACAAGTG GATACGAACA TCGCAATGAT TCATGCGGCA
2821 GATAAACGCG TTCATAGAAT CCGGGAAGCG TATCTGCCAG AGTTGTCTGT GATTCCAGGT
2881 GTCAATGCGG CCATTTTCGA AGAATTAGAG GGACGTATTT TTACAGCGTA TTCCTTATAT
2941 GATGCGAGAA ATGTCATTAA AAATGGCGAT TTCAATAATG GCTTATTATG CTGGAACGTG

           3010       3020       3030       3040       3050       3060
3001 AAAGGTCATG TAGATGTAGA AGAGCAAAAC AACCACCGTT CGGTCCTTGT TATCCCAGAA
3061 TGGGAGGCAG AAGTGTCACA AGAGGTTCGT GTCTGTCCAG GTCGTGGCTA TATCCTTCGT
3121 GTCACAGCAT ATAAAGAGGG ATATGGAGAG GGCTGCGTAA CGATCCATGA GATCGAAGAC
3181 AATACAGACG AACTGAAATT CAGCAACTGT GTAGAAGAGG AAGTATATCC AAACAACACA
3241 GTAACGTGTA ATAATTATAC TGGGACTCAA GAAGAATATG AGGGTACGTA CACTTCTCGT

           3310       3320       3330       3340       3350       3360
3301 AATCAAGGAT ATGACGAAGC CTATGGTAAT AACCCTTCCG TACCAGCTGA TTACGCTTCA
3361 GTCTATGAAG AAAAATCGTA TACAGATGGA CGAAGAGAGA ATCCTTGTGA ATCTAACAGA
3421 GGCTATGGGG ATTACACACC ACTACCGGCT GGTTATGTAA CAAAGGATTT AGAGTACTTC
3481 CCAGAGACCG ATAAGGTATG GATTGAGATC GGAGAAACAG AAGGAACATT CATCGTGGAT
3541 AGCGTGGAAT TACTCCTTAT GGAGGAA
```

Segment 1-*

Figure 8D

```
                          5                                      10                                      15
  1 Met Glu Glu Asn Asn Gln Asn Gln Cys Ile Pro Tyr Asn Cys Leu
 16 Ser Asn Pro Glu Glu Val Leu Leu Asp Gly Glu Arg Ile Ser Thr
 31 Gly Asn Ser Ser Ile Asp Ile Ser Leu Ser Leu Val Gln Phe Leu
 46 Val Ser Asn Phe Val Pro Gly Gly Gly Phe Leu Val Gly Leu Ile
 61 Asp Phe Val Trp Gly Ile Val Gly Pro Ser Gln Trp Asp Ala Phe
 76 Leu Val Gln Ile Glu Gln Leu Ile Asn Glu Arg Ile Ala Glu Phe
 91 Ala Arg Asn Ala Ala Ile Ala Asn Leu Glu Gly Leu Gly Asn Asn
106 Phe Asn Ile Tyr Val Glu Ala Phe Lys Glu Trp Glu Glu Asp Pro
121 Asn Asn Pro Ala Thr Arg Thr Arg Val Ile Asp Arg Phe Arg Ile
136 Leu Asp Gly Leu Leu Glu Arg Asp Ile Pro Ser Phe Arg Ile Ser
151 Gly Phe Glu Val Pro Leu Leu Ser Val Tyr Ala Gln Ala Ala Asn
166 Leu His Leu Ala Ile Leu Arg Asp Ser Val Ile Phe Gly Glu Arg
181 Trp Gly Leu Thr Thr Ile Asn Val Asn Glu Asn Tyr Asn Arg Leu
196 Ile Arg His Ile Asp Glu Tyr Ala Asp His Cys Ala Asn Thr Tyr
211 Asn Arg Gly Leu Asn Asn Leu Pro Lys Ser Thr Tyr Gln Asp Trp
```

Figure 9A

```
226 Ile Thr Tyr Asn Arg Leu Arg Arg Asp Leu Thr Leu Thr Val Leu
241 Asp Ile Ala Ala Phe Phe Pro Asn Tyr Asp Asn Arg Arg Tyr Pro
256 Ile Gln Pro Val Gly Gln Leu Thr Arg Glu Val Tyr Thr Asp Pro
271 Leu Ile Asn Phe Asn Pro Gln Leu Gln Ser Val Ala Gln Leu Pro
286 Thr Phe Asn Val Met Glu Ser Ser Ala Ile Arg Asn Pro His Leu
301 Phe Asp Ile Leu Asn Asn Leu Thr Ile Phe Thr Asp Trp Phe Ser
316 Val Gly Arg Asn Phe Tyr Trp Gly Gly His Arg Val Ile Ser Ser
331 Leu Ile Gly Gly Gly Asn Ile Thr Ser Pro Ile Tyr Gly Arg Glu
346 Ala Asn Gln Glu Pro Pro Arg Ser Phe Thr Phe Asn Gly Pro Val
361 Phe Arg Thr Leu Ser Asn Pro Thr Leu Arg Leu Leu Gln Gln Pro
376 Trp Pro Ala Pro Pro Phe Asn Leu Arg Gly Val Glu Gly Val Glu
391 Phe Ser Thr Pro Thr Asn Ser Phe Thr Tyr Arg Gly Arg Gly Thr
406 Val Asp Ser Leu Thr Glu Leu Pro Pro Glu Asp Asn Ser Val Pro
421 Pro Arg Glu Gly Tyr Ser His Arg Leu Cys His Ala Thr Phe Val
436 Gln Arg Ser Gly Thr Pro Phe Leu Thr Thr Gly Val Val Phe Ser
```

Figure 9B

```
451 Trp Thr His Arg Ser Ala Thr Leu Thr Asn Thr Ile Asp Pro Glu
466 Arg Ile Asn Gln Ile Pro Leu Val Lys Gly Phe Arg Val Trp Gly
481 Gly Thr Ser Val Ile Thr Gly Pro Gly Phe Thr Gly Gly Asp Ile
496 Leu Arg Arg Asn Thr Phe Gly Asp Phe Val Ser Leu Gln Val Asn
511 Ile Asn Ser Pro Ile Thr Gln Arg Tyr Arg Leu Arg Phe Arg Tyr
526 Ala Ser Ser Arg Asp Ala Arg Val Ile Val Leu Thr Gly Ala Ala
541 Ser Thr Gly Val Gly Gly Gln Val Ser Val Asn Met Pro Leu Gln
556 Lys Thr Met Glu Ile Gly Glu Asn Leu Thr Ser Arg Thr Phe Arg
571 Tyr Thr Asp Phe Ser Asn Pro Phe Ser Phe Arg Ala Asn Pro Asp
586 Ile Ile Gly Ile Ser Glu Gln Pro Leu Phe Gly Ala Gly Ser Ile
601 Ser Ser Gly Glu Leu Tyr Ile Asp Lys Ile Glu Ile Ile Leu Ala
616 Asp Ala Thr Phe Glu Ala Glu Ser Asp Leu Glu Arg Ala Gln Lys
631 Ala Val Asn Ala Leu Phe Thr Ser Ser Asn Gln Ile Gly Leu Lys
646 Thr Asp Val Thr Asp Tyr His Ile Asp Gln Val Ser Asn Leu Val
661 Asp Cys Leu Ser Asp Glu Phe Cys Leu Asp Glu Lys Arg Glu Leu
```

Figure 9C

```
676 Ser Glu Lys Val Lys His Ala Lys Arg Leu Ser Asp Glu Arg Asn
691 Leu Leu Gln Asp Pro Asn Phe Arg Gly Ile Asn Arg Gln Pro Asp
706 Arg Gly Trp Arg Gly Ser Thr Asp Ile Thr Ile Gln Gly Gly Asp
721 Asp Val Phe Lys Glu Asn Tyr Val Thr Leu Pro Gly Thr Val Asp
736 Glu Cys Tyr Pro Thr Tyr Leu Tyr Gln Lys Ile Asp Glu Ser Lys
751 Leu Lys Ala Tyr Thr Arg Tyr Glu Leu Arg Gly Tyr Ile Glu Asp
766 Ser Gln Asp Leu Glu Ile Tyr Leu Ile Arg Tyr Asn Ala Lys His
781 Glu Ile Val Asn Val Pro Gly Thr Gly Ser Leu Trp Pro Leu Ser
796 Ala Gln Ser Pro Ile Gly Lys Cys Gly Glu Pro Asn Arg Cys Ala
811 Pro His Leu Glu Trp Asn Pro Asp Leu Asp Cys Ser Cys Arg Asp

826 Gly Glu Lys Cys Ala His His Ser His His Phe Thr Leu Asp Ile
841 Asp Val Gly Cys Thr Asp Leu Asn Glu Asp Leu Gly Val Trp Val
856 Ile Phe Lys Ile Lys Thr Gln Asp Gly His Ala Arg Leu Gly Asn
871 Leu Glu Phe Leu Glu Glu Lys Pro Leu Leu Gly Glu Ala Leu Ala
886 Arg Val Lys Arg Ala Glu Lys Lys Trp Arg Asp Lys Arg Glu Lys
```

Figure 9D

```
 901 Leu Gln Leu Glu Thr Asn Ile Val Tyr Lys Glu Ala Lys Glu Ser
 916 Val Asp Ala Leu Phe Val Asn Ser Gln Tyr Asp Arg Leu Gln Val
 931 Asp Thr Asn Ile Ala Met Ile His Ala Ala Asp Lys Arg Val His
 946 Arg Ile Arg Glu Ala Tyr Leu Pro Glu Leu Ser Val Ile Pro Gly
 961 Val Asn Ala Ala Ile Phe Glu Glu Leu Glu Gly Arg Ile Phe Thr
 976 Ala Tyr Ser Leu Tyr Asp Ala Arg Asn Val Ile Lys Asn Gly Asp
 991 Phe Asn Asn Gly Leu Leu Cys Trp Asn Val Lys Gly His Val Asp
1006 Val Glu Glu Gln Asn Asn His Arg Ser Val Leu Val Ile Pro Glu
1021 Trp Glu Ala Glu Val Ser Gln Glu Val Arg Val Cys Pro Gly Arg
1036 Gly Tyr Ile Leu Arg Val Thr Ala Tyr Lys Glu Gly Tyr Gly Glu
1051 Gly Cys Val Thr Ile His Glu Ile Glu Asp Asn Thr Asp Glu Leu
1066 Lys Phe Ser Asn Cys Val Glu Glu Glu Val Tyr Pro Asn Asn Thr
1081 Val Thr Cys Asn Asn Tyr Thr Gly Thr Gln Glu Glu Tyr Glu Gly
1096 Thr Tyr Thr Ser Arg Asn Gln Gly Tyr Asp Glu Ala Tyr Gly Asn
1111 Asn Pro Ser Val Pro Ala Asp Tyr Ala Ser Val Tyr Glu Glu Lys
1126 Ser Tyr Thr Asp Gly Arg Arg Glu Asn Pro Cys Glu Ser Asn Arg
1141 Gly Tyr Gly Asp Tyr Thr Pro Leu Pro Ala Gly Tyr Val Thr Lys
1156 Asp Leu Glu Tyr Phe Pro Glu Thr Asp Lys Val Trp Ile Glu Ile
1171 Gly Glu Thr Glu Gly Thr Phe Ile Val Asp Ser Val Glu Leu Leu
1186 Leu Met Glu Glu
```

Fragment 1-*

Figure 9E

```
                    5                   10                  15                  20
Met Glu Glu Asn Asn Gln Asn Gln Cys Ile Pro Tyr Asn Cys Leu Ser Asn Pro Glu Glu
ATG GAG GAA AAT AAT CAA AAT CAA TGC ATA CCT TAC AAT TGT TTA AGT AAT CCT GAA GAA

                   25                   30                  35                  40
Val Leu Leu Asp Gly Glu Arg Ile Ser Thr Gly Asn Ser Ser Ile Asp Ile Ser Leu Ser
GTA CTT TTG GAT GGA GAA CGG ATA TCA ACT GGT AAT TCA TCA ATT GAT ATT TCT CTG TCA

                   45                   50                  55                  60
Leu Val Gln Phe Leu Val Ser Asn Phe Val Pro Gly Gly Gly Phe Leu Val Gly Leu Ile
CTT GTT CAG TTT CTG GTA TCT AAC TTT GTA CCA GGG GGA GGA TTT TTA GTT GGA TTA ATA

                   65                   70                  75                  80
Asp Phe Val Trp Gly Ile Val Gly Pro Ser Gln Trp Asp Ala Phe Leu Val Gln Ile Glu
GAT TTT GTA TGG GGA ATA GTT GGC CCT TCT CAA TGG GAT GCA TTT CTA GTA CAA ATT GAA
```

Figure 10A

```
                    85                  90                  95                 100
Gln Leu Ile Asn Glu Arg Ile Ala Glu Phe Ala Arg Asn Ala Ala Ile Ala Asn Leu Glu
CAA TTA ATT AAT GAA AGA ATA GCT GAA TTT GCT AGG AAT GCT GCT ATT GCT AAT TTA GAA

                   105                 110                 115                 120
Gly Leu Gly Asn Asn Phe Asn Ile Tyr Val Glu Ala Phe Lys Glu Trp Glu Glu Asp Pro
GGA TTA GGA AAC AAT TTC AAT ATA TAT GTG GAA GCA TTT AAA GAA TGG GAA GAA GAT CCT

                   125                 130                 135                 140
Asn Asn Pro Ala Thr Arg Thr Arg Val Ile Asp Arg Phe Arg Ile Leu Asp Gly Leu Leu
AAT AAT CCA GCA ACC AGG ACC AGA GTA ATT GAT CGC TTT CGT ATA CTT GAT GGG CTA CTT

                   145                 150                 155                 160
Glu Arg Asp Ile Pro Ser Phe Arg Ile Ser Gly Phe Glu Val Pro Leu Leu Ser Val Tyr
GAA AGG GAC ATT CCT TCG TTT CGA ATT TCT GGA TTT GAA GTA CCC CTT TTA TCC GTT TAT

                   165                 170                 175                 180
Ala Gln Ala Ala Asn Leu His Leu Ala Ile Leu Arg Asp Ser Val Ile Phe Gly Glu Arg
GCT CAA GCG GCC AAT CTG CAT CTA GCT ATA TTA AGA GAT TCT GTA ATT TTT GGA GAA AGA
```

Figure 10B

```
                185                 190                 195                 200
Trp Gly Leu Thr Thr Ile Asn Val Asn Glu Asn Tyr Asn Arg Leu Ile Arg His Ile Asp
TGG GGA TTG ACA ACG ATA AAT GTC AAT GAA AAC TAT AAT AGA CTA ATT AGG CAT ATT GAT

                205                 210                 215                 220
Glu Tyr Ala Asp His Cys Ala Asn Thr Tyr Asn Arg Gly Leu Asn Asn Leu Pro Lys Ser
GAA TAT GCT GAT CAC TGT GCA AAT ACG TAT AAT CGG GGA TTA AAT AAT TTA CCG AAA TCT

                225                 230                 235                 240
Thr Tyr Gln Asp Trp Ile Thr Tyr Asn Arg Leu Arg Arg Asp Leu Thr Leu Thr Val Leu
ACG TAT CAA GAT TGG ATA ACA TAT AAT CGA TTA CGG AGA GAC TTA ACA TTG ACT GTA TTA

                245                 250                 255                 260
Asp Ile Ala Ala Phe Phe Pro Asn Tyr Asp Asn Arg Arg Tyr Pro Ile Gln Pro Val Gly
GAT ATC GCC GCT TTC TTT CCA AAC TAT GAC AAT AGG AGA TAT CCA ATT CAG CCA GTT GGT

                265                 270                 275                 280
Gln Leu Thr Arg Glu Val Tyr Thr Asp Pro Leu Ile Asn Phe Asn Pro Gln Leu Gln Ser
CAA CTA ACA AGG GAA GTT TAT ACG GAC CCA TTA ATT AAT TTT AAT CCA CAG TTA CAG TCT
```

Figure 10C

```
                    285                     290                     295                     300
Val Ala Gln Leu Pro Thr Phe Asn Val Met Glu Ser Ser Ala Ile Arg Asn Pro His Leu
GTA GCT CAA TTA CCT ACT TTT AAC GTT ATG GAG AGC AGC GCA ATT AGA AAT CCT CAT TTA

                    305                     310                     315                     320
Phe Asp Ile Leu Asn Asn Leu Thr Ile Phe Thr Asp Trp Phe Ser Val Gly Arg Asn Phe
TTT GAT ATA TTG AAT AAT CTT ACA ATC TTT ACG GAT TGG TTT AGT GTT GGA CGC AAT TTT

                    325                     330                     335                     340
Tyr Trp Gly Gly His Arg Val Ile Ser Ser Leu Ile Gly Gly Gly Asn Ile Thr Ser Pro
TAT TGG GGA GGA CAT CGA GTA ATA TCT AGC CTT ATA GGA GGT GGT AAC ATA ACA TCT CCT

                    345                     350                     355                     360
Ile Tyr Gly Arg Glu Ala Asn Gln Glu Pro Pro Arg Ser Phe Thr Phe Asn Gly Pro Val
ATA TAT GGA AGA GAG GCG AAC CAG GAG CCT CCA AGA TCC TTT ACT TTT AAT GGA CCG GTA

                    365                     370                     375                     380
Phe Arg Thr Leu Ser Asn Pro Thr Leu Arg Leu Leu Gln Gln Pro Trp Pro Ala Pro Pro
TTT AGG ACT TTA TCA AAT CCT ACT TTA CGA TTA TTA CAG CAA CCT TGG CCA GCG CCA CCA
```

Figure 10D

```
                  385                 390                           395                           400
Asn Leu Arg Gly Val Glu Gly Val Glu Phe Ser Thr Pro Thr Asn Ser Ser Phe Thr Tyr
AAT TTA CGT GGT GTT GAA GGA GTA GAA TTT TCT ACA CCT ACA AAT AGC AGC TTT ACG TAT

                  405                 410                           415                           420
Gly Arg Gly Thr Val Asp Ser Leu Thr Glu Leu Pro Pro Glu Asp Asn Ssn Ser Val Pro
GGA AGA GGT ACG GTT GAT TCT TTA ACT GAA TTA CCG CCT GAG GAT AAT AAT AGT GTG CCA

                  425                 430                           435                           440
Arg Glu Gly Tyr Ser His Arg Leu Cys His Ala Thr Phe Val Gln Arg Srg Ser Gly Thr
CGC GAA GGA TAT AGT CAT CGT TTA TGT CAT GCA ACT TTT GTT CAA AGA AGA TCT GGA ACA

                  445                 450                           455                           460
Phe Leu Thr Thr Gly Val Val Phe Ser Trp Thr His Arg Ser Ala Thr Thr Leu Thr Asn
TTT TTA ACA ACT GGT GTA GTA TTT TCT TGG ACG CAT CGT AGT GCA ACT CCT CTT ACA AAT

                  465                 470                           475                           480
Ile Asp Pro Glu Arg Ile Asn Gln Ile Pro Leu Val Lys Gly Phe Arg Vrg Val Trp Gly
ATT GAT CCA GAG AGA ATT AAT CAA ATA CCT TTA GTG AAA GGA TTT AGA GGA GTT TGG GGG
```

Figure 10E

```
                485                 490                 495                 500
Thr Ser Val Val Ile Thr Gly Pro Gly Phe Thr Gly Gly Asp Ile Leu Arg Arg Asn Thr
ACC TCT GTC GTC ATT ACA GGA CCA GGA TTT ACA GGA GGG GAT ATC CTT CGA AGA AAT ACC

                505                 510                 515                 520
Gly Asp Phe Phe Val Ser Leu Gln Val Asn Ile Asn Ser Pro Ile Thr Gln Arg Tyr Arg
GGT GAT TTT TTT GTA TCT CTA CAA GTC AAT ATT AAT TCA CCA ATT ACC CAA AGA TAC CGT

                525                 530                 535                 540
Arg Phe Arg Arg Tyr Ala Ser Ser Arg Asp Ala Arg Val Ile Val Leu Thr Gly Ala Ala
AGA TTT CGT CGT TAC GCT TCC AGT AGG GAT GCA CGA GTT ATA GTA TTA ACA GGA GCG GCA

                545                 550                 555                 560
Thr Gly Val Val Gly Gly Gln Val Ser Val Asn Met Pro Leu Gln Lys Thr Met Glu Ile
ACA GGA GTG GTG GGA GGC CAA GTT AGT GTA AAT ATG CCT CTT CAG AAA ACT ATG GAA ATA

                565                 570                 575                 580
Glu Asn Leu Leu Thr Ser Arg Thr Phe Arg Tyr Thr Asp Phe Ser Asn Pro Phe Ser Phe
GAG AAC TTA TTA ACA TCT AGA ACA TTT AGA TAT ACC GAT TTT AGT AAT CCT TTT TCA TTT
```

Figure 10F

```
                585                 590                 595                 600
Arg Ala Asn Pro Asp Ile Ile Gly Ile Ser Glu Gln Pro Leu Phe Gly Ala Gly Ser Ile
AGA GCT AAT CCA GAT ATA ATT GGG ATA AGT GAA CAA CCT CTA TTT GGT GCA GGT TCT ATT

                605                 610                 615                 620
Ser Ser Gly Glu Leu Tyr Ile Asp Lys Ile Glu Ile Ile Leu Ala Asp Ala Thr Phe Glu
AGT AGC GGT GAA CTT TAT ATA GAT AAA ATT GAA ATT ATT CTA GCA GAT GCA ACA TTT GAA

                625                 630                 635                 640
Ala Glu Ser Asp Leu Glu Arg Ala Gln Lys Ala Val Asn Ala Leu Phe Thr Ser Ser Asn
GCA GAA TCT GAT TTA GAA AGA GCA CAA AAG GCG GTG AAT GCC CTG TTT ACT TCT TCC AAT

                645                 650                 655                 660
Gln Ile Gly Leu Lys Thr Asp Val Thr Asp Tyr His Ile Asp Gln Val Ser Asn Leu Val
CAA ATC GGG TTA AAA ACC GAT GTG ACG GAT TAT CAT ATT GAT CAA GTA TCC AAT TTA GTG

                665                 670                 675                 680
Asp Cys Leu Ser Asp Glu Phe Cys Leu Asp Glu Lys Arg Glu Leu Ser Glu Lys Val Lys
GAT TGT TTA TCA GAT GAA TTT TGT CTG GAT GAA AAG CGA GAA TTG TCC GAG AAA GTC AAA
```

Figure 10G

```
                685                 690                                     695                         700
Ala Lys Arg Leu Ser Asp Glu Arg Asn Leu Leu Gln Asn Asp Pro Asn Phe Arg Gly Ile
GCG AAG CGA CTC AGT GAT GAG CGG AAT TTA CTT CAA GAA GAT CCA AAC TTC AGA GGG ATC

                705                 710                                     715                         720
Arg Gln Pro Asp Arg Gly Trp Arg Gly Ser Thr Asp Ilp Ile Thr Ile Gln Gly Gly Asp
AGA CAA CCA GAC CGT GGC TGG AGA GGA AGT ACA GAT ATT ATT ACC ATC CAA GGA GGA GAT

                725                 730                                     735                         740
Val Phe Lys Glu Asn Tyr Val Thr Leu Pro Gly Thr Var Val Asp Glu Cys Tyr Pro Thr
GTA TTC AAA GAG AAT TAC GTC ACA CTA CCG GGT ACC GTC GTT GAT GAG TGC TAT CCA ACG

                745                 750                                     755                         760
Leu Tyr Gln Lys Ile Asp Glu Ser Lys Leu Lys Ala Tya Tyr Thr Arg Tyr Glu Leu Arg
TTA TAT CAG AAA ATA GAT GAG TCG AAA TTA AAA GCT TAT TAT ACC CGT TAT GAA TTA AGA

                765                 770                                     775                         780
Tyr Ile Glu Asp Ser Gln Asp Leu Glu Ile Tyr Leu Ilu Ile Arg Tyr Asn Ala Lys His
TAT ATC GAA GAT AGT CAA GAC TTA GAA ATC TAT TTG ATG ATC CGT TAC AAT GCA AAA CAC
```

Figure 10H

```
                    785                 790                 795                 800
Glu Ile Val Asn Val Pro Gly Thr Gly Ser Leu Trp Pro Leu Ser Ala Gln Ser Pro Ile
GAA ATA GTA AAT GTG CCA GGC ACG GGT TCC TTA TGG CCG CTT TCA GCC CAA AGT CCA ATC

                    805                 810                 815                 820
Gly Lys Cys Gly Glu Pro Asn Arg Cys Ala Pro His Leu Glu Trp Asn Pro Asp Leu Asp
GGA AAG TGT GGA GAA CCG AAT CGA TGC GCG CCA CAC CTT GAA TGG AAT CCT GAT CTA GAT

                    825                 830                 835                 840
Cys Ser Cys Arg Asp Gly Glu Lys Cys Ala His His Ser His His Phe Thr Leu Asp Ile
TGT TCC TGC AGA GAC GGG GAA AAA TGT GCA CAT CAT TCC CAT CAT TTC ACC TTG GAT ATT

                    845                 850                 855                 860
Asp Val Gly Cys Thr Asp Leu Asn Glu Asp Leu Gly Val Trp Val Ile Phe Lys Ile Lys
GAT GTT GGA TGT ACA GAC TTA AAT GAG GAC TTA GGT GTA TGG GTG ATA TTC AAG ATT AAG

                    865                 870                 875                 880
Thr Gln Asp Gly His Ala Arg Leu Gly Asn Leu Glu Phe Leu Glu Glu Lys Pro Leu Leu
ACG CAA GAT GGC CAT GCA AGA CTA GGG AAT CTA GAG TTT CTC GAA GAG AAA CCA TTA TTA
```

Figure 10I

```
                885                 890                 895                 900
Gly Glu Ala Leu Ala Arg Val Lys Arg Ala Glu Lys Lys Trp Arg Asp Lys Arg Glu Lys
GGG GAA GCA CTA GCT CGT GTG AAA AGA GCG GAG AAG AAG TGG AGA GAC AAA CGA GAG AAA

                905                 910                 915                 920
Leu Gln Leu Glu Thr Asn Ile Val Tyr Lys Glu Ala Lys Glu Ser Val Asp Ala Leu Phe
CTG CAG TTG GAA ACA AAT ATT GTT TAT AAA GAG GCA AAA GAA TCT GTA GAT GCT TTA TTT

                925                 930                 935                 940
Val Asn Ser Gln Tyr Asp Arg Leu Gln Val Asp Thr Asn Ile Ala Met Ile His Ala Ala
GTA AAC TCT CAA TAT GAT AGA TTA CAA GTG GAT ACG AAC ATC GCA ATG ATT CAT GCG GCA

                945                 950                 955                 960
Asp Lys Arg Val His Arg Ile Arg Glu Ala Tyr Leu Pro Glu Leu Ser Val Ile Pro Gly
GAT AAA CGC GTT CAT AGA ATC CGG GAA GCG TAT CTG CCA GAG TTG TCT GTG ATT CCA GGT

                965                 970                 975                 980
Val Asn Ala Ala Ile Phe Glu Glu Leu Glu Gly Arg Ile Phe Thr Ala Tyr Ser Leu Tyr
GTC AAT GCG GCC ATT TTC GAA GAA TTA GAG GGA CGT ATT TTT ACA GCG TAT TCC TTA TAT
```

Figure 10J

```
                    985                 990                      995                     1000
Asp Ala Arg Asn Val Ile Lys Asn Gly Asp Phe Asn Asn Gly Leu Leu Cys Trp Asn Val
GAT GCG AGA AAT GTC ATT AAA AAT GGC GAT TTC AAT AAT GGC TTA TTA TGC TGG AAC GTG

                   1005                1010                     1015                     1020
Lys Gly His Val Asp Val Glu Glu Gln Asn Asn His Arg Ser Val Leu Val Ile Pro Glu
AAA GGT CAT GTA GAT GTA GAA GAG CAA AAC AAC CAC CGT TCG GTC CTT GTT ATC CCA GAA

                   1025                1030                     1035                     1040
Trp Glu Ala Glu Val Ser Gln Glu Val Arg Val Cys Pro Gly Arg Gly Tyr Ile Leu Arg
TGG GAG GCA GAA GTG TCA CAA GAG GTT CGT GTC TGT CCA GGT CGT GGC TAT ATC CTT CGT

                   1045                1050                     1055                     1060
Val Thr Ala Tyr Lys Glu Gly Tyr Gly Glu Gly Cys Val Thr Ile His Glu Ile Glu Asp
GTC ACA GCA TAT AAA GAG GGA TAT GGA GAG GGC TGC GTA ACG ATC CAT GAG ATC GAA GAC

                   1065                1070                     1075                     1080
Asn Thr Asp Glu Leu Lys Phe Ser Asn Cys Val Glu Glu Glu Val Tyr Pro Asn Asn Thr
AAT ACA GAC GAA CTG AAA TTC AGC AAC TGT GTA GAA GAG GAA GTA TAT CCA AAC AAC ACA
```

Figure 10K

```
                        1085                     1090                      1095                       1100
Val Thr Cys Asn Asn Tyr Thr Gly Thr Gln Glu Glu Tyr Glu Gly Thr Tyr Thr Ser Arg
GTA ACG TGT AAT AAT TAT ACT GGG ACT CAA GAA GAA TAT GAG GGT ACG TAC ACT TCT CGT

                        1105                     1110                      1115                       1120
Asn Gln Gly Tyr Asp Glu Ala Tyr Gly Asn Asn Pro Ser Val Pro Ala Asp Tyr Ala Ser
AAT CAA GGA TAT GAC GAA GCC TAT GGT AAT AAC CCT TCC GTA CCA GCT GAT TAC GCT TCA

                        1125                     1130                      1135                       1140
Val Tyr Glu Glu Lys Ser Tyr Thr Asp Gly Arg Arg Glu Asn Pro Cys Glu Ser Asn Arg
GTC TAT GAA GAA AAA TCG TAT ACA GAT GGA CGA AGA GAG AAT CCT TGT GAA TCT AAC AGA

                        1145                     1150                      1155                       1160
Gly Tyr Gly Asp Tyr Thr Pro Leu Pro Ala Gly Tyr Val Thr Lys Asp Leu Glu Tyr Phe
GGC TAT GGG GAT TAC ACA CCA CTA CCG GCT GGT TAT GTA ACA AAG GAT TTA GAG TAC TTC

                        1165                     1170                      1175                       1180
Pro Glu Thr Asp Lys Val Trp Ile Glu Ile Gly Glu Thr Glu Gly Thr Phe Ile Val Asp
CCA GAG ACC GAT AAG GTA TGG ATT GAG ATC GGA GAA ACA GAA GGA ACA TTC ATC GTG GAT
                        1185
Ser Val Glu Leu Leu Leu Met Glu Glu
AGC GTG GAA TTA CTC CTT ATG GAG GAA
```

Figure 10L

BACILLUS THURINGIENSIS ISOLATE ACTIVE AGAINST LEPIDOPTERAN PESTS, AND GENES ENCODING NOVEL LEPIDOPTERAN-ACTIVE TOXINS

This is a division, of application Ser. No. 07/371,955, filed Jun. 27, 1989, now U.S. Pat. No. 5,126,133.

BACKGROUND OF THE INVENTION

The most widely used microbial pesticides are derived from the bacterium *Bacillus thuringiensis*. This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. kurstaki HD-1 produces a crystal inclusion consisting of a biotoxin called a delta toxin which is toxic to the larvae of a number of lepidopteran insects. The cloning, sequencing, and expression of this *B.t.* crystal protein gene in *Escherichia coli* has been described in the published literature (Schnepf, H. E. and Whitely, H. R. [1981] Proc. Natl. Acad. Sci. USA 78:2893–2897; Schnepf et al.). U.S. Pat. No. 4,448,885 and U.S. Pat. No. 4,467,036 both disclose the expression of *B.t.* crystal protein in *E. coli*.

BRIEF SUMMARY OF THE INVENTION

The subject invention concerns a novel *Bacillus thuringiensis* isolate designated *B.t.* PS81I which has activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises the novel *B.t.* isolate denoted *B.t.* PS81I, mutants thereof, and novel δ-endotoxin genes derived from this *B.t.* isolate which encode proteins which are active against lepidopteran pests.

BRIEF DESCRIPTION OF THE DRAWINGS

FIGS. 2A–2D—Nucleotide Sequence of toxin gene 81IA2.

FIGS. 3A–3E—Deduced amino acid sequence of toxin expressed by toxin gene 81IA2.

FIGS. 4A–4L—Composite of FIGS. 2 and 3.

FIGS. 5A–5D—Nucleotide sequence of the toxin gene 81IB.

FIGS. 6A–6E—Deduced amino acid sequence of toxin expressed by toxin gene 81IB.

FIGS. 7A–7L—Composite of FIGS. 5 and 6.

FIGS. 8A–8D—Nucleotide sequence of the toxin gene 81IB2.

FIGS. 9A–9E—Deduced amino acid sequence of toxin expressed by toxin gene 81IB2.

FIGS. 10A–10L—Composite of FIGS. 8 and 9.

DETAILED DISCLOSURE OF THE INVENTION

Figure 1:
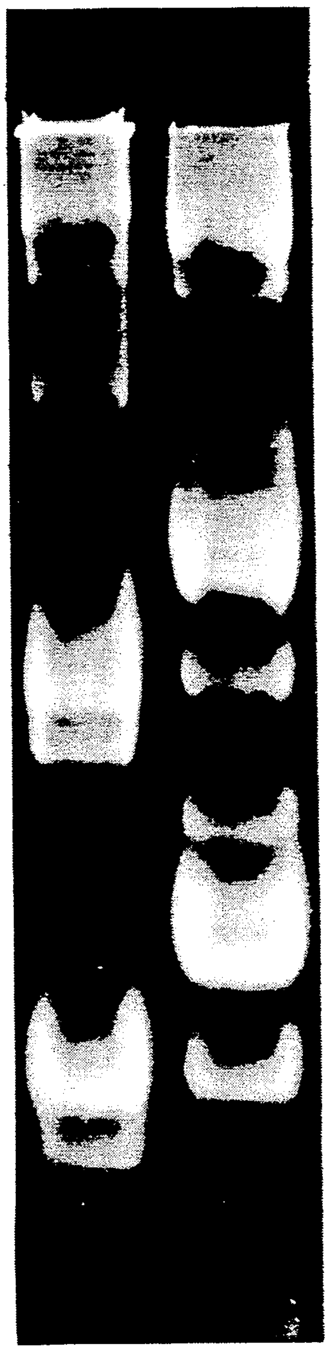
FIG. 1—agarose gel electrophoresis of plasmid preparations from *B.t.* HD-1 and *B.t.* PS81I.

The novel toxin genes of the subject invention were obtained from a novel lepidopteran-active *B. thuringiensis* (*B.t.*) isolate designated PS81I.

Characteristics of *B.t.* PS81I

Colony morphology—Large colony, dull surface, typical *B.t.*

Vegetative cell morphology—typical *B.t.*

Flagellar serotype—7, aizawai.

Intracellular inclusions—sporulating cells produce a bipyramidal crystal.

Plasmid preparations—agarose gel electrophoresis of plasmid preparations distinguishing *B.t.* PS81I from *B.t.* HD-1. See FIG. 1.

Alkali-soluble proteins—SDS-PAGE analysis shows a protein band at ca. 130,000 daltons.

Unique toxins—four unique toxins have been identified in *B.t.* PS81I.

Activity—*B.t.* PS81I kills all Lepidoptera tested.

Bioassay procedures:

*B.t.* PS81I spores and crystals were tested against: Beet Armyworm, *Spodoptera exigua*; Diamondback Moth, *Plutella xylostella*; Western Spruce Budworm, *Choristoneura occidentalis*.

LC50 values were as follows:

Beet Armyworm—2.53 ppm

Diamondback Moth—0.16 ppm

Western Spruce Budworm—3.2 ppm

Bioassay procedure: dilutions are prepared of a spore and crystal pellet, mixed with USDA Insect Diet (Technical Bulletin 1528, U.S. Department of Agriculture), and poured into small plastic trays. Larvae are placed on the diet mixture and held at 25° C. (late 2nd instar Diamondback Moth larvae, early 2nd instar Beet Armyworm larvae, 4th instar Western Spruce Budworm larvae). Mortality is recorded after six days.

*B. thuringiensis* PS81I, NRRL B-18484, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against *Lepidoptera*, e.g., caterpillars. *B.t.* PS81I, and mutants thereof, can be used to control lepidopteran pests.

A subculture of *B.t.* PS81I and the *E. coli* hosts harboring the toxin genes of the invention, were deposited in the permanent collection of the Northern Research Laboratory, U.S. Department of Agriculture, Peoria, Ill., USA. The accession numbers and deposit dates are as follows:

| Subculture | Accession Number | Deposit Date |
|---|---|---|
| *B.t.* PS81I | NRRL B-18484 | April 19, 1989 |
| *E. coli* (NM522)(pMYC392) | NRRL B-18498 | May 17, 1989 |
| *E. coli* (NM522)(pMYC393) | NRRL B-18499 | May 17, 1989 |
| *E. coli* (NM522)(pMYC394) | NRRL B-18500 | May 17, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing a *B.t.* gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances to higher organsisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eugkaryotes are fungi, such as Phycomycetes and Ascomycetes, which includes yest, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formulation of inclusion bodies; leaf affinity; lack of mammaliam toxicity; attractiveness to pests for ingestion; ease of killing and fixing without damage to the toxin; and the like. Other consideration include ease of formulation and handling, economics, storage stability, and the like.

Host organisms of particular interest include yeast, such as Rhodotorula sp., Aureobasidium sp., Saccaromyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; antiinfectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W.H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81I can be made by procedures well known in the art. For example, an asporogenous mutant can be obtained through ethylmethane sulfonate (EMS) mutagenesis of PS81I. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogeneous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* PS81I

A subculture of *B.t.* PS81I, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

-continued

| pH 7.2 |
|---|

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Genes From Isolate PS81I and Transformation into *Escherichia coli*

Total cellular DNA was prepared from B.t. cells grown to a low optical density ($OD_{600}$=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81I and B.t.k. HD-1 was digested with EcoRI and separated by electrophoresis on a 0.8% (w/v) Agarose-TAE (50 mM Tris-Cl, 20 mM NaOAc, 2.5 mM EDTA, pH=8.0) buffered gel. A Southern blot of the gel was hybridized with a [$^{32}$P] radiolabeled probe against the 3.2 Kb NsiI to NsiI fragment of the toxin gene contained in plasmid pM3,130-7 of NRRL B-18332 and the 2.4 Kb NsiI to KpnI fragment of the "4.5 Kb class" toxin gene (Kronstad and Whitely [1986] Gene USA 43:29–40). These two fragments were combined and used as the probe. Results show that hybridizing fragments of PS81I are distinct from those of HD-1. Specifically, in the 1.5 Kb to 2.5 Kb size range, 2.3 Kb, 1.95 Kb, and 1.6 Kb hybridizing bands were detected in PS81I instead of the single 1.9 Kb hybridizing band in HD-1.

The following description outlines the steps taken in cloning two of the three EcoRI fragments described above. Two hundred micrograms of PS81I total cellular DNA was digested with EcoRI and separated by electrophoresis on a preparative 0.8% (w/v) Agarose-TAE gel. The 1.5 Kb to 2.3 Kb region of the gel was cut out and the DNA from it was electroeluted and concentrated using an ELUTIP™-d (Schleicher and Schuell, Keene, NH) ion exchange column according to the manufacturer's specification. The isolated EcoRI fragments were ligated to LAMBDA ZAP™ EcoRI arms (Stratagene Cloning Systems, La Jolla, CA) and packaged using Gigapak GOLD™ (Stratagene) extracts. The packaged recombinant phage were plated with *E. coli* strain BB4 (Stratagene) to give high plaque density. The plaques were screened by standard nucleic acid hybridization procedures with radiolabeled probe. The plaques that hybridized were purified and re-screened at a lower plaque density. The resulting purified phage were grown with R408 M13 helper phage (Stratagene) and the recombinant BlueScript™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by a standard rapid plasmid purification procedure to identify the desired plasmids. The plasmids, designated pM2,31-4 and pM2,31-1, contain approximately 1.95 Kb and 1.6 Kb EcoRI inserts, respectively. The DNA sequence of both inserts was determined using Stratagene's T7 and T3 oligonucleotide primers plus a set of existing internal *B.t.* endotoxin gene oligonucleotide primers. About 500 bp of the insert in pM2,31-4 was sequenced. In the same manner, approximately 1.0 Kb of the insert in pM2,31-1 was sequenced. Data analysis comparing the two sequences to other cloned and sequenced *B.t.* endotoxin genes showed that two distinct, unique partial toxin gene sequences had been found. Synthetic oligonucleotides were constructed to regions in both sequences that had minimum homology to other characterized *B.t.* endotoxin genes. The 42-mer oligonucleotide constructed to the sequence of the insert in pM2,31-4 was GGATACCGGTGACCCATTAACATTCCAATCTTTTAGTTACGC; it was used to isolate a toxin gene sequence called 81IA. The 40-mer oligonucleotide constructed to the sequence of the insert in pM2,31-1 was GAAGTTTATGGCCTCTTTCTGTAGAAAATCAAATTGGACC; it was used to isolate a toxin gene sequence called 81IB.

In order to clone both complete toxin genes, a Sau3A partial library was constructed. PS81I total cellular DNA partially digested with Sau3A and size fractionated by electrophoresis into a mixture of 9-23 Kb fragments on a 0.6% agarose-TAE gel, and purified as described previously, was ligated into LambdaGEM-11™ (PROMEGA). The packaged phage were plated on P2392 *E. coli* cells (Stratagene) at a high titer and screened using the radiolabeled synthetic oligonucleotides (aforementioned) as nucleic acid hybridization probes. Hybridizing plaques, using each probe, were rescreened at a lower plaque density. Purified plaques that hybridized with either probe were used to infect P2392 *E. coli* cells in liquid culture for preparation of phage for DNA isolation. DNA was isolated by standard procedures. Preparative amounts of DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pUC19 (NEB). The ligation mix was introduced by transformation into DH5(α) competent *E. coli* cells (BRL) and plated on LB agar containing ampicillin, isopropyl-(β)-D-thiogalactoside (IPTG), and 5-bromo-4-chloro-3-indolyl-(β)-D-galactoside (XGAL). White colonies, with prospective insertions in the (β)-galactosidase gene of pUC19, were subjected to standard rapid plasmid purification procedures to isolate the desired plasmids. Plasmid pM3,122-1 contains a 15 Kb Sau3A fragment isolated using the 81IA oligonucleotide probe. Plasmid pM4,59-1 contains an 18 Kb Sau3A fragment isolated using the 81IB oligonucleotide probe.

Plasmid pM3,122-1 was digested with several restriction enzymes and Southern blotted. The blot was probed with the [$^{32}$P] radiolabeled 81IA specific oligonucleotide probe, as well as the labeled oligonucleotide sequencing primers made to known B.t. k. toxin genes. The resulting autoradiogram showed that two toxin genes were present in tandem on this cloned Sau3A fragment. Plasmid pM3,122-1 had a 4.0 Kb NdeI fragment that hybridized with oligonucleotide probes made to known B.t.k. genes. This fragment, however, did not hybridize with the specific oligonucleotides to 81IA or 81IB; a new toxin gene had been discovered and subsequently was called 81IA2. The 4.0 Kb NdeI fragment was isolated and cloned in pUC19, yielding plasmid pMYC392. The 81IA toxin gene was isolated by digesting pM3,122-1 with HindIII, with resulting deletion of most of the 81IA2 toxin gene. The fragment was recircularized to form pMYC1603. The 81IA toxin gene is unique based on its restriction map and is presently being sequenced.

Plasmid pM4,59-1 was digested with several restriction enzymes and Southern blotted. The blot was probed with the [$^{32}$P] radiolabeled 81IB specific oligonucleotide probe, as well as with labeled oligonucleotide sequencing primers made to known B.t.k. toxin genes. The plasmid pM4,59-1 was mapped and found to contain only a partial 81IB toxin gene. The full open reading frame (ORF) of a second toxin gene was discovered on the 18 Kb fragment and called 81IB2. The 81IB2 toxin gene was cloned separately from the 81IB toxin gene by digestion of pM4,59-1 with NdeI and SmaI, filling in the NdeI overhang and ligating the linear fragment back together. The resulting plasmid was called pMYC394. The full ORF of the 81IB toxin gene was isolated from another Sau3A fragment, cloned from the lambda library, on a 7.3 Kb HindIII fragment in pBluescript (Stratagene). The resulting plasmid is pMYC393.

The toxin genes were sequenced by the standard Sanger dideoxy chain termination method using oligonucleotide primers made to the "4.5 Kb class" toxin gene and by "walking" with primers made to the sequences of the new toxin genes. Sequence analysis of three toxin genes has elucidated three unique open reading frames and has deduced three unique endotoxin proteins (FIGS. 2-10). The following table summarizes the size of each ORF in base pairs and the deduced endotoxin molecular weight in daltons.

| TOXIN GENE | ORF (bp) | DEDUCED MW (daltons) | FIG. |
|---|---|---|---|
| 81IA2 | 3537 | 133,397 | 2-4 |
| 81IB | 3495 | 132,480 | 5-7 |
| 81IB2 | 3567 | 134,714 | 8-10 |

An endotoxin protein has been expressed in Pseudomonas and/or Bacillus from the three cloned and sequenced toxin genes. SDS-PAGE/Western blot analysis, using polyclonal antibodies directed against the "6.6 Kb" class toxin, verified that each gene encodes an immunoreactive protein of approximately 130,000 daltons. The toxin proteins encoded by genes 81IA, 81IB, and 81IB2 expressed in either a Bacillus or Pseudomonas host have activity against all lepidopteran insects tested: *Trichoplusia ni, Spodoptera exigua, Plutella xylostella*, and *Choristoneura occidentalis*.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., New England Biolabs, Beverly, Mass., or Boehringer-Mannheim, Indianapolis, Ind. The enzymes are used according to the instructions provided by the supplier.

The plasmids containing the *B.t.* toxin genes can be removed from the transformed host microbes by use of standard well-known procedures. For example, the host microbes can be subjected to cleared lysate isopycnic density gradient procedures, and the like, to recover the desired plasmid.

EXAMPLE 3

Insertion of Toxin Genes Into Plants

The novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *B. thuringiensis* Genes Into Baculoviruses

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al. (Smith, G. E., Summers, M. D. and Fraser, M. J. [1983] Mol. Cell. Biol. 3:2156-2165). The gene coding for the novel protein toxin of the invention can be modified with BamHI linkers at appropriate reqions both upstream and downstream from the coding region and inserted into the passenger site of one of the AcNPV vectors.

As disclosed previously, the nucleotide sequences encoding the novel *B.t.* toxin genes are shown in FIGS.

2, 5 and 8. The deduced amino acid sequences are shown in FIGS. 3, 6 and 9.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalinine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W—C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequences of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

We claim:

1. An isolated DNA encoding a *Bacillus thuringiensis* toxin having an amino acid sequence selected from the group consisting of the amino acid sequence shown in FIG. 3, FIG. 6, and FIG. 9.

2. An isolated DNA according to claim 1, encoding the amino acid sequence shown in FIG. 3.

3. An isolated DNA according to claim 1, encoding the amino acid sequence shown in FIG. 6.

4. An isolated DNA according to claim 1, encoding the amino acid sequence shown in FIG. 9.

5. An isolated DNA encoding a *Bacillus thuringiensis* toxin, said DNA having a nucleotide sequence selected from the group consisting of the sequences shown in FIG. 2, FIG. 5 and FIG. 8.

6. An isolated DNA according to claim 5, encoding the amino acid sequence shown in FIG. 2.

7. An isolated DNA according to claim 5, encoding the amino acid sequence shown in FIG. 5.

8. An isolated DNA according to claim 5, encoding the amino acid sequence shown in FIG. 8.

9. A recombinant DNA transfer vector comprising DNA having all or part of the nucleotide sequence which codes for a toxin having an amino acid sequence selected from the group consisting of the sequences shown in FIG. 3, FIG. 6 and FIG. 9.

10. The vector comprising DNA, according to claim 9, wherein said DNA has the sequence shown in FIG. 3.

11. The vector comprising DNA, according to claim 9, wherein said DNA has the sequence shown in FIG. 6.

12. The vector comprising DNA, according to claim 9, wherein said DNA has the sequence shown in FIG. 9.

13. The DNA transfer vector, according to claim 9, transferred to and replicated in a prokaryotic or eukaryotic host.

14. A plasmid selected from the group consisting of pMYC392, pMYC393, and pMYC394.

15. A bacterial host transformed to express a *Bacillus thuringiensis* toxin having an amino acid sequence selected from the group consisting of the sequence shown in FIG. 3, FIG. 6 and FIG. 9.

16. The bacterial host containing a toxin, according to claim 15, wherein said toxin has the sequence shown in FIG. 3.

17. The bacterial host containing a toxin, according to claim 15, wherein said toxin has the sequence shown in FIG. 6.

18. The bacterial host containing a toxin, according to claim 15, wherein said toxin has the sequence shown in FIG. 9.

19. *Escherichia coli* transformed with a plasmid vector containing a *Bacillus thuringiensis* toxin gene encoding a *Bacillus thuringiensis* toxin having an amino acid sequence selected from the group consisting of the sequence shown in FIG. 3, FIG. 6, and FIG. 9.

20. The *Escherichia coli* transformed to express a toxin, according to claim 19, wherein said toxin has the amino acid sequence shown in FIG. 3.

21. The *Escherichia coli* transformed to express a toxin, according to claim 19, wherein said toxin has the amino acid sequence shown in FIG. 6.

22. The *Escherichia coli* transformed to express a toxin, according to claim 19, wherein said toxin has the amino acid sequence shown in FIG. 9.

23. A transformed host selected from the group consisting of *Escherichia coli* (NM522)(pMYC392), having the identifying characteristics of NRRL B-18498, *Escherichia coli* (NM522)(pMYC393), having the identifying characteristics of NRRL B-18499, and *Escherichia coli* (NM522)(pMYC394), having the identifying characteristics of NRRL B-18500.

24. A microorganism according to claim 15, which is a species of Pseudomonas, Azotobacter, Erwinia, Serratia, Klebsiella, Rhizobium, Rhodopseudomonas, Methylophilius, Agrobacterium, Acetobacter, Alcaligenes, Bacillus, or Streptomyces.

25. A microorganism according to claim 24, wherein said microorganism is pigmented and phylloplane adherent.

26. A treated, substantially intact unicellular microorganism cell containing an intracellular toxin, which toxin is a result of expression of a *Bacillus thuringiensis* toxin gene toxic to lepidopteran insects which codes for a polypeptide toxin having an amino acid sequence selected from the group consisting of the sequence shown in FIG. 3, FIG. 6, and FIG. 9, wherein said cell is treated under conditions which prolong the insecticidal activity when said cell is applied in a plurality to the environment of a target insect.

27. The cell, according to claim 26, wherein the cell is treated by chemical or physical means to prolong its insecticidal activity in the environment.

28. The cell according to claim 26, wherein said microorganism is Pseudomonas and said toxin is a *Bacillus thuringiensis* toxin having an amino acid sequence selected from the group consisting of the sequence shown in FIG. 3, FIG. 6, and FIG. 9.

29. The cell containing a toxin, according to claim 28, wherein said toxin has the amino acid sequence shown in FIG. 3.

30. The cell containing a toxin, according to claim 28, wherein said toxin has the amino acid sequence shown in FIG. 6.

31. The cell containing a toxin, according to claim 28, wherein said toxin has the amino acid sequence shown in FIG. 9.

32. A Pseudomonas cell according to claim 28, wherein said cells is treated with iodine.

33. The cell, according to claim 26, which are *Pseudomonas fluorescens.*

34. An insecticidal composition comprising insecticide containing substantially intact, treated cells having prolonged pesticidal activity when applied to the environment of a target pest, wherein said insecticide is a polypeptide toxic to lepidopteran insects, is intracellular, and is produced as a result of expression of a transformed microbe capable of expressing a *Bacillus thuringiensis* toxin having an amino acid sequence selected from the group consisting of the sequence shown in FIG. 3, FIG. 6, and FIG. 9.

35. The insecticidal composition, according to claim 34, wherein said amino acid sequence is shown in FIG. 3.

36. The insecticidal composition, according to claim 34, wherein said amino acid sequence is shown in FIG. 6.

37. The insecticidal composition, according to claim 34, wherein said amino acid sequence is shown in FIG. 9.

38. The insecticidal composition, according to claim 34, wherein said treated cells are treated by chemical or physical means to prolong their insecticidal activity in the environment.

39. The insecticidal composition, according to claim 38, wherein said cells are prokaryotes or lower eukaryotes.

40. The insecticidal composition, according to claim 39, wherein said prokaryotic cells are selected form the group consisting of Pseudomonas, Azotobacter, Erwinia, Serratia, Klebsiella, Rhizobium, Rhodopseudomonas, Methylophilius, Agrobacterium, Acetobacter, Alcaligenes, Bacillus, and Streptomyces.

41. The insecticidal composition, according to claim 39, wherein said lower eukaryotic cells are selected from the group consisting of a fungal host and a yeast host.

42. The insecticidal composition, according to claim 34, wherein said cell is a pigmented bacterium, yeast, or fungus.

* * * * *

UNITED STATES PATENT AND TRADEMARK OFFICE

CERTIFICATE OF CORRECTION

PATENT NO. : 5,246,852

DATED : September 21, 1993

INVENTOR(S) : Jewel Payne and August J. Sick

It is certified that error appears in the above-indentified patent and that said Letters Patent is hereby corrected as shown below:

Column 6 line 20: After "substances" insert --toxic--.

Column 6 line 33: Delete "eugkaryotes" and insert --eukaryotes--.

Column 6 line 35: Delete "yest" and insert --yeast--.

Column 6 line 47: Delete "formulation" and insert --formation--.

Signed and Sealed this

Nineteenth Day of April, 1994

Attest:

BRUCE LEHMAN

*Attesting Officer* *Commissioner of Patents and Trademarks*